(12) United States Patent
Zhang et al.

(10) Patent No.: US 10,336,713 B2
(45) Date of Patent: Jul. 2, 2019

(54) TRIAZOLE-BASED READER MOLECULES AND METHODS FOR SYNTHESIZING AND USE THEREOF

(71) Applicant: Arizona Board of Regents, Acting for and on behalf of, Arizona State University, Scottsdale, AZ (US)

(72) Inventors: Peiming Zhang, Gilbert, AZ (US); Stuart Lindsay, Phoenix, AZ (US); Sovan Biswas, Tempe, AZ (US); Suman Sen, Tempe, AZ (US)

(73) Assignee: Arizona Board of Regents, Acting for and on behalf of, Arizona State University, Scottsdale, AZ (US)

( * ) Notice: Subject to any disclaimer, the term of this patent is extended or adjusted under 35 U.S.C. 154(b) by 0 days.

(21) Appl. No.: 15/121,669

(22) PCT Filed: Feb. 27, 2015

(86) PCT No.: PCT/US2015/018062
§ 371 (c)(1),
(2) Date: Aug. 25, 2016

(87) PCT Pub. No.: WO2015/131073
PCT Pub. Date: Sep. 3, 2015

(65) Prior Publication Data
US 2016/0362384 A1 Dec. 15, 2016

Related U.S. Application Data

(60) Provisional application No. 61/945,659, filed on Feb. 27, 2014.

(51) Int. Cl.
*G01N 33/487* (2006.01)
*C12Q 1/00* (2006.01)
(Continued)

(52) U.S. Cl.
CPC .......... *C07D 249/10* (2013.01); *C07C 319/12* (2013.01); *G01N 27/3276* (2013.01)

(58) Field of Classification Search
CPC .......... G01N 27/3276; G01N 27/3275; G01N 33/48721; G01N 33/5438; G01N 27/327;
(Continued)

(56) References Cited

U.S. PATENT DOCUMENTS 3,619,206 A  11/1971  Laurence et al.
4,804,707 A   2/1989  Okamoto et al.
(Continued)

FOREIGN PATENT DOCUMENTS

WO   1992001476    2/1992
WO   20010192890  12/2001
(Continued)

OTHER PUBLICATIONS

Lee et al., "Reactivity of Acetylenyl-Terminated Self-Assembled Monolayers on Gold: Triazole Formation", Langmuir 2004, 20, pp. 3844-3847. (Year: 2004).*
(Continued)

*Primary Examiner* — Thanh Truc Trinh
(74) *Attorney, Agent, or Firm* — Schwabe Williamson & Wyatt, P.C.

(57) ABSTRACT

Triazole-based molecules, methods of making and using the same are provided. Triazole-based molecules may be used as reading molecules and incorporated into or operatively-linked with electrodes, for example, and used in recognition tunneling systems to identify individual and/or sequences of molecules (e.g., DNA bases, carbohydrates, proteins, peptides, and/or amino-acids).

12 Claims, 19 Drawing Sheets

(51) Int. Cl.
*C07D 249/10* (2006.01)
*G01N 27/327* (2006.01)
*C07C 319/12* (2006.01)

(58) Field of Classification Search
CPC ..... C07C 31/12; C07D 249/10; Y10T 156/10; C12Q 1/001; C12Q 1/006
USPC ...... 436/94; 422/82.01; 156/60; 204/403.01, 204/403.14
See application file for complete search history.

(56) References Cited

U.S. PATENT DOCUMENTS

| | | |
|---|---|---|
| 5,066,716 A | 11/1991 | Robey et al. |
| 5,879,436 A | 3/1999 | Kramer et al. |
| 6,215,798 B1 | 4/2001 | Carneheim et al. |
| 6,537,755 B1 | 3/2003 | Drmanac |
| 6,627,067 B1 | 9/2003 | Branton et al. |
| 6,821,730 B2 | 11/2004 | Hannah |
| 6,824,974 B2 | 11/2004 | Pisharody et al. |
| 6,905,586 B2 | 6/2005 | Lee et al. |
| 7,001,792 B2 | 2/2006 | Sauer et al. |
| 7,033,476 B2 | 4/2006 | Lee et al. |
| 7,282,130 B2 | 10/2007 | Flory |
| 7,638,034 B2 | 12/2009 | Sansinena et al. |
| 7,700,306 B2 | 4/2010 | Thompson et al. |
| 8,003,319 B2 | 8/2011 | Polonsky et al. |
| 8,278,055 B2 | 10/2012 | Su et al. |
| 8,628,649 B2 | 1/2014 | Lindsay et al. |
| 2002/0033345 A1 | 3/2002 | Meade |
| 2002/0117659 A1 | 8/2002 | Lieber et al. |
| 2003/0089605 A1 | 5/2003 | Timperman |
| 2003/0099951 A1 | 5/2003 | Akeson et al. |
| 2003/0148289 A1 | 8/2003 | Sundararajan et al. |
| 2003/0203394 A1 | 11/2003 | Eichen et al. |
| 2003/0215376 A1 | 11/2003 | Chopra |
| 2004/0128081 A1 | 7/2004 | Rabitz et al. |
| 2004/0144658 A1 | 7/2004 | Flory |
| 2004/0262636 A1 | 12/2004 | Yang et al. |
| 2005/0032053 A1 | 2/2005 | Sampson |
| 2005/0095599 A1 | 5/2005 | Pittaro et al. |
| 2005/0136408 A1 | 6/2005 | Tom-Moy et al. |
| 2005/0202444 A1 | 9/2005 | Zhu |
| 2005/0217990 A1 | 10/2005 | Sibbett et al. |
| 2006/0073489 A1 | 4/2006 | Li et al. |
| 2006/0194228 A1 | 8/2006 | Rakitin et al. |
| 2006/0211016 A1 | 9/2006 | Kayyem et al. |
| 2006/0263255 A1 | 11/2006 | Han et al. |
| 2007/0009379 A1 | 1/2007 | Bau et al. |
| 2007/0154890 A1 | 7/2007 | Isobe |
| 2007/0292855 A1 | 12/2007 | Dubin et al. |
| 2008/0050752 A1 | 2/2008 | Sun et al. |
| 2008/0121534 A1 | 5/2008 | White et al. |
| 2008/0171316 A1 | 7/2008 | Golovchenko et al. |
| 2009/0198117 A1 | 8/2009 | Cooper et al. |
| 2009/0298072 A1 | 12/2009 | Ju et al. |
| 2009/0308741 A1 | 12/2009 | Frey et al. |
| 2009/0309614 A1 | 12/2009 | Goodman et al. |
| 2009/0326238 A1 | 12/2009 | Bum et al. |
| 2010/0084276 A1 | 4/2010 | Lindsay |
| 2010/0145626 A1 | 6/2010 | Ecker et al. |
| 2010/0294659 A1 | 11/2010 | Green |
| 2010/0031042 A1 | 12/2010 | Oliver et al. |
| 2011/0065164 A1 | 3/2011 | Santoyo Gonzalez et al. |
| 2011/0070735 A1 | 3/2011 | Shi |
| 2011/0120868 A1 | 5/2011 | Lindsay et al. |
| 2011/0124118 A1 | 5/2011 | Park et al. |
| 2011/0168562 A1 | 7/2011 | Nuckolls et al. |
| 2011/0258409 A1 | 11/2011 | Maleki et al. |
| 2012/0097539 A1 | 4/2012 | Qian et al. |
| 2012/0288935 A1 | 11/2012 | Mirkin et al. |
| 2012/0288948 A1 | 11/2012 | Lindsay et al. |
| 2012/0329741 A1 | 12/2012 | Oyelere et al. |
| 2012/0330001 A1 | 12/2012 | Darzins et al. |
| 2013/0186757 A1 | 7/2013 | Reinhart et al. |
| 2013/0302901 A1 | 11/2013 | Lindsay et al. |
| 2013/0316912 A1 | 11/2013 | Bjornson et al. |
| 2014/0005509 A1 | 1/2014 | Bhavaraju et al. |

FOREIGN PATENT DOCUMENTS

| | | |
|---|---|---|
| WO | 2010042514 | 4/2010 |
| WO | 2011097171 | 8/2011 |
| WO | 2013116509 | 8/2013 |
| WO | 2013123379 | 8/2013 |
| WO | 2013148344 | 10/2013 |
| WO | 2013180819 | 12/2013 |
| WO | 2015131073 | 9/2015 |

OTHER PUBLICATIONS

Klewer et al., "Conformation of Nucleoside Analogue 1-(2'-Deoxy-b-D-ribofuranosyl)-1,2,4-triazole-3-carboxamide in Different DNA Sequence Contexts"), Biochemistry 2001, 40, 1518-1527. (Year: 2001).*
Tsutsui M, Taniguchi M, Yokota K, Kawai T. Identifying single nucleotides by tunnelling current. Nat Nanotechnol 2010, 5(4): 286-290.
Tuchband M, He J, Huang S, Lindsay S. Insulated gold scanning tunneling microscopy probes for recognition tunneling in an aqueous environment. Rev Sci Instrum 83, 015102 (2012).
Xu B, Zhang P, Li X, Tao N. Direct Conductance Measurement of Single DNA Molecules in Aqueous Solution. Nano letters 2004, 4(6): 1105-1108.
Yakovchuk P, Protozanova E, Frank-Kamenetskii MD. Base-stacking and base-pairing contributions into thermal stability of the DNA double helix. Nucleic Acids Res. 2006, 34(2): 564-574.
Zhao Y, Ashcroft B, Zhang P, Liu H, Sen S, Song W, et al. Single-molecule spectroscopy of amino acids and peptides by recognition tunnelling. Nature Nanotechnology 2014, 9: 466-473.
Zwolak- M, Ventra MD. Electronic Signature of DNA Nucleotides via Transverse Transport. Nano Lett 2005, 5(3): 421-424.
Branton, et al. The Potential and Challenges of Nanopore Sequencing. Nat. Biotechnol. 26.10(2008):1146-1153.
Bacri, L. et al., Discrimination of neutral oligosaccharides through a nanopore, Biochemical and Biophysical Research Communications 2011, vol. 412, No. 4, pp. 561-564.
Chang, S. et al, Electronic Signatures of all Four DNA Nucleosides in a Tunneling Gap, Nano Lett., 10:1070-1075, 2010.
Chang et al., Tunneling readout of hydrogen-bonding based recognition, Nature Nanotechnology, May 2009, 4(5):297-301.
Clarke et al., Continuous base identification for single-molecule nanopore DNA sequencing, Nature Nanotechnology, Apr. 2009, 4(4):265-270.
Derose et al, Comparative scanning prove microscopy study of the surface morphology of Au films grown from the vapor onto glass, fused silica, and muscovite mica, Journal of Vacuum Science & Technology, A 11(4), 776-780, Jul./Aug. 1993.
Derrington et al., Nanopore DNA sequencing with MspA, Proc. Natl. Aca. Sci, USA, Sep. 14, 2010, vol. 107, No. 37, 16060-16065.
Friddle et al., Near-Equilibrium Chemical Force Microscopy, J. Phys. Chem. C 2008, 112, 4986-4990, publication date (web): Mar. 8, 2008.
Fuhrmann et al., In vivo fluorescence imaging of exogenous enzyme activity in the gastrointestinal tract, PNAS, May 31, 2011, vol. 108, No. 22, 9032-9037.
Lindsay, S. et al., Recognition Tunneling, Nanotechnology, Jul. 2, 2010; 21(26): 262001.
Muthukumar et al., Simulation of Polymer Translocation Through Protein Channels, published online Mar. 27, 2006, PNAS vol. 103, No. 14, 5273-5278, Apr. 4, 2006.
Mohammad, M. et al., Controlling a Single Protein in a Nanopore through Electrostatic Traps, published (web) Mar. 6, 2008, Journal of the American Chemical Society 2008, vol. 130, No. 12, pp. 4081-4088.
Nivala, J. et al., Unfoldase-mediated protein translocation through an alpha-hemolysin nanopore, published online Feb. 3, 2013, Nature Biotechnology 31, pp. 247-250 (2013).

(56) References Cited

OTHER PUBLICATIONS

Pathak et al., Double-functionalized nanopore-embedded gold electrodes for rapid DNA sequencing, Applied Physics Letters 100, 023701, 2012, published online Jan. 9, 2012.
Saha et al., DNA base-specific modulation of µA transverse edge currents through a metallic graphene nanoribbon with a nanopore, published Dec. 5, 2011, Nano Lett. 2012, 12, 50-55.
Tsutsui, M. et al., Single-molecule identification via electric current noise, published Dec. 14, 2010, Nature Communications, 1:138, DOI: 101038.
Tsutsui, M. et al., Single-molecule sensing electrode embedded in-plane nanopore, Jul. 28, 2011, Scientific Reports, 1:46, DOI: 101038.
Visoly-Fisher, I. et al., Conductance of a biomolecular wire, Proc. Nat. Acad. Sci., Jun. 6, 2006, vol. 103, No. 23, 8686-8690.
Zwolak, et al. Colloquium: Physical Approaches to DNA Sequencing and Detection, published Jan. 2, 2008, Reviews of Modern Physics, vol. 80, No. 1, Jan.-Mar. 2008, 141-165.
Gracheva, M. E. et al., Simulation of the electric response of DNA translocation through a semiconductor nanopore-capacitor, published Jan. 6, 2006, Nanotechnology 17 (2006), 622-633.
Graham, R. S. et al., Coarse-grained brownian dynamics simulations of electrophoresis of DNA molecules from generalized reptation models, published (web) Dec. 15, 2006, Macromolecules 2007, vol. 40, No. 2, 366-378.
International Search Report and Written Opinion for PCT Application PCT/US2013/032113 filed on Mar. 15, 2013.
International Search Report and Written Opinion for PCT Application PCT/US2013/024130 filed on Jan. 31, 2013.
International Search Report and Written Opinion for PCT Application PCT/US2013/032346 filed on Mar. 15, 2013.
International Search Report and Written Opinion for PCT Application PCT/US2014/020789 filed on Mar. 5, 2014.
International Search Report and Written Opinion for PCT Application PCT/US2014/040323 filed on May 30, 2014.
International Search Report and Written Opinion for PCT Application PCT/US2015/018062 filed on Feb. 27, 2015.
Aradi et al., DFTB+, a Sparse Matrix-Based Implementation of the DFTB Method. The Journal of Physical Chemistry. A., 2007, 111: 5678-5684.
Bano et al., Unraveling the complexity of the interactions of DNA nucleotides with gold by single molecule force spectroscopy. Nanoscale, 2015, 7(46): 19528-19533.
Cancer Genome Atlas Research Network. Comprehensive genomic characterization of squamous cell lung cancers. Nature, 2012, 489(7417): 519-525.
Dario AD, Pecchia A, Latessa L, Frauenheim T, Seifert G. Tight-binding DFT for molecular electronics (gDFTB) Introducing Molecular Electronics. In: Introducing Molecular Electronics: Lecture Notes in Physics (Editors: Cuniberti G, Fagas G, Richter K). Springer (2005) vol. 680: p. 153-184.
Chan EY. Next-Generation Sequencing Methods: Impact of Sequencing Accuracy on SNP discovery. In: Komar AA (ed). Single Nucleotide Polymorphism. Method in Molecular Biology, vol. 578, 2009, pp. 95-111.
Chang et al., Chemical recognition and binding kinetics in a functionalized tunnel junction. Nanotechnology, 2012, 23(23): 235101.
Chang et al., Palladium electrodes for molecular tunnel junctions. Nanotechnology, 2012, 23(42): 425202.
Chang et al., Gap distance and interactions in a molecular tunnel junction. Journal of the American Chemical Society, 2011, 133(36): 14267-14269.
Datta, Electrical resistance: an atomistic view. Nanotechnology, 2004, 15, S433-S451.
Elstner et al., Self-consistent-charge density-functional tight-binding method for simulations of complex materials properties. Physical Review B, 1998, 58(11):7260-7268.
Erdmann et al., Electrically induced bonding of DNA to gold. Nature Chemistry, 2010, 2(9): 745-749.
Frampton et al., Development and validation of a clinical cancer genomic profiling test based on massively parallel DNA sequencing. Nature Biotechnology, 2013, 31(11): 1023-1031.
Goodwin et al., Coming of age: ten years of next-generation sequencing technologies. Nature Reviews Genetics, 2016, 17, 333-351.
Grimme, Do special noncovalent pi-pi stacking interactions really exist? Angewandte Chemie (International Edition) Engl. 2008, 47(18): 3430-3434.
Guckian KM, Schweitzer BA, Ren RX-F, Sheils CJ, Tahmassebi DC, Kool ET. Factors Contributing to Aromatic Stacking in Water: Evaluation in the Context of DNA. Journal of the American Chemical Society, 2000, 122(10): 2213-2222.
Huang et al., Fidelity and predominant mutations produced by deep vent wild-type and exonuclease-deficient DNA polymerases during in vitro DNA amplification. DNA and Cell Biology, 1996, 15(7): 589-594.
Huang S, He J, Chang S, Zhang P, Liang F, Li S, et al. Identifying single bases in a DNA oligomer with electron tunnelling. Nature Nanotechnology 2010, 5: 868-873.
Im J, Biswas S, Liu H, Zhao Y, Sen S, Biswas S, et al. Electronic Single Molecule Identification of Carbohydrate Isomers by Recognition Tunneling. arXiv 2016: 1601.04221.
Jain M, Fiddes IT, Miga KH, Olsen HE, Paten B, Akeson M. Improved data analysis for the MinION nanopore sequencer. Nat Methods 2015, 12(4): 351-356.
Jünemann S, Sedlazeck FJ, Prior K, Albersmeier A, John U, Kalinowski Jr, et al. Updating benchtop sequencing performance comparison. Nat. Biotechnol. 2013, 31: 294-296.
Kelley SO, Barton JK. Electron Transfer Between Bases in Double Helical DNA. Science 283, 375-381 (1999).
Kimura-Suda H, Petrovykh DY, Tarlov MJ, Whitman LJ. Base-Dependent Competitive Adsorption of Single-Stranded DNA on Gold. J. Am. Chem. Soc. 2003, 125: 9014-9015.
Lai JS, Qu J, Kool ET. Fluorinated DNA bases as probes of electrostatic effects in DNA base stacking. Angew. Chem. Int. Ed. Engl. 2003, 42(48): 5973-5977.
Laszlo AH, Derrington IM, Ross BC, Brinkerhoff H, Adey A, Nova IC, et al. Decoding long nanopore sequencing reads of natural DNA. Nat Biotechnol. 2014, 32(8): 829-833.
Laver T, et al. Assessing the performance of the Oxford Nanopore Technologies MinION. Biomolecular Detection and Quantrfication 3, 1-8 (2015).
Li Z, Nakagawa O, Koga Y, Taniguchi Y, Sasaki S. Synthesis of new derivatives of 8-oxoG-clamp for better understanding the recognition mode and improvement of selective affinity. Bioorg Med Chem 18, 3992-3998 (2010).
Liang F, Li S, Lindsay S, Zhang P. Synthesis, physicochemical properties, and hydrogen bonding of 4(5)-substituted 1-H-imidazole-2-carboxamide, a potential universal reader for DNA sequencing by recognition tunneling. Chemistry (Easton) 2012, 18(19): 5998-6007.
Lindsay S. The promises and challenges of solid-state sequencing. Nat Nanotechnol 2016, 11(2): 109-111.
Liu L, Li Y, Li S, Hu N, He Y, Pong R, et al. Comparison of next-generation sequencing systems. J Biomed Biotechnol 2012, 2012: 251364.
Madoui M-A, Engelen S, Cruaud C, Belse C, Bertrand L, Alberti A, et al. Genome assembly using Nanopore-guided ong and error-free DNA reads. MC Genomics 2015, 16: 327.
Manrao EA, Derrington IM, Laszlo AH, Langford KW, Hopper MK, Gillgren N, et al. Reading DNA at single-nucleotide resolution with a mutant MspA nanopore and phi29 DNA polymerase. Nat. Biotechnol. 2012, 30(4): 349-353.
Martincorena Ii, Campbell PJ. Somatic mutation in cancer and normal cells. Science 2015, 349: 1483-1489.
Mukhopadhyay R. DNA sequencers: the next generation. Anal. Chem. 2009, 81(5): 1736-1740.
Ohshiro T, Matsubara K, Tsutsui M, Furuhashi M, Taniguchi M, Kawai T. Single-molecule electrical random resequencing of DNA and RNA. Sci Rep 2, 501 (2012).

(56) References Cited

OTHER PUBLICATIONS

Paez JG, Lin M, Beroukhim R, Lee JC, Zhao X, Richter DJ, et al. Genome coverage and sequence fidelity of phi29 polymerase-based multiple strand displacement whole genome amplification. Nucleic Acids Res. 2004, 32(9): e71.

Sang P, Ashcroft BA, Song W, Zhang P, Biswas S, Qing Q, et al. Fixed-Gap Tunnel Junction for Reading DNA Nucleotides. ACS nano 2014, 8(12): 11994-12003.

Patra A, Zhang Q, Lei L, Su Y, Egli M, Guengerich FP. Structural and kinetic analysis of nucleoside triphosphate incorporation opposite an abasic site by human translesion DNA polymerase eta. J Biol Chem 290, 8028-8038 (2015).

Pecchia A, Carlo AD. Atomistic theory of transport in organic and inorganic nanostructures. Reports on Progress in Physics 67, 1497-1561 (2004).

Pecchia A, Penazzi G, Salvucci L, Di Carlo A. Non-equilibrium Green's functions in density functional tight binding: method and applications. New Journal of Physics 10, 065022 (2008).

Petersheimf M, Turner DH. Base-Stacking and Base-Pairing Contributions to Helix Stability: Thermodynamics of Double-Helix Formation with CCGG, CCGGp, CCGGAp, ACCGGp, CCGGUp, and ACCGGUp. Biochemistry 22, 256-263 (1983).

Porezag D, Frauenheim T, Köhler T, Seifert G, Kaschner R. Construction of tight-binding-like potentials on the basis of density-functional theory: Application to carbon. Physical Review B 51, 12947-12957 (1995).

Qi Y, Liu X, Liu CG, Wang B, Hess KR, Symmans WF, et al. Reproducibility of Variant Calls in Replicate Next Generation Sequencing Experiments. PLoS One 2015, 10(7): e0119230.

Riley KE, Hobza PH. On the Importance and Origin of Aromatic Interactions in Chemistry and Biodisciplines. Accounts of Chemical Research 2013, 46(4): 927-936.

Robasky K, Lewis NE, Church GM. The role of replicates for error mitigation in next-generation sequencing. Nat Rev Genet 2014, 15(1): 56-62.

Ross JS, Wang K, Gay L, Otto GA, White E, Iwanik K, et al. Comprehensive Genomic Profiling of Carcinoma of Unknown Primary Site: New Routes to Targeted Therapies. JAMA Oncol 2015, 1(1): 40-49.

Ross JS, Wang K, Khaira D, Ali SM, Fisher HA, Mian B, et al. Comprehensive genomic profiling of 295 cases of clinically advanced urothelial carcinoma of the urinary bladder reveals a high frequency of clinically relevant genomic alterations. Cancer 2016, 122(5): 702-711.

Strauss BS. The "A" rule revisited: polymerases as determinants of mutational specificity. DNA Repair 1, 125-135 (2002).

Swart M, van der Wijst T, Fonseca Guerra C, Bickelhaupt FM. Pi-pi stacking tackled with density functional theory. J. Mol. Model. 2007, 13(12): 1245-1257.

Szalay T, Golovchenko JA. De novo sequencing and variant calling with nanopores using PoreSeq. Nat. Biotechnol. 2015, 33(10): 1087-1091.

Treangen TJ, Salzberg SL. Repetitive DNA and next-generation sequencing: computational challenges and solutions. Nat Rev Genet 2011, 13(1): 36-46.

Biswas, S., et al. "Universal Readers Based on Hydrogen Bonding or π-π Stacking for Identification of DNA Nucleotide in Electron Tunnel Junctions", in ACS Nano, 2016, pp. 11304-11316.

\* cited by examiner 3-(2-mercaptoethyl)-1H-1,2,4-triazole-5-carboxamide ⇌ 5-(2-mercaptoethyl)-1H-1,2,4-triazole-3-carboxamide ⇌ 5-(2-mercaptoethyl)-4H-1,2,4-triazole-3-carboxamide

| Atom | % in XPS | Ratio in XPS | Expected ratio |
|---|---|---|---|
| S | 5.52 | 1 | 1 |
| C | 26.90 | 4.87 | 5 |
| N | 20.71 | 3.75 | 4 |

| Triazole modified Pd substrate (°) | Bare Pd substrate (°) |
|---|---|
| 35 ± 4 | 9 ± 2 |

TCA at 4pA

ICA at 4pA

Figure 8A
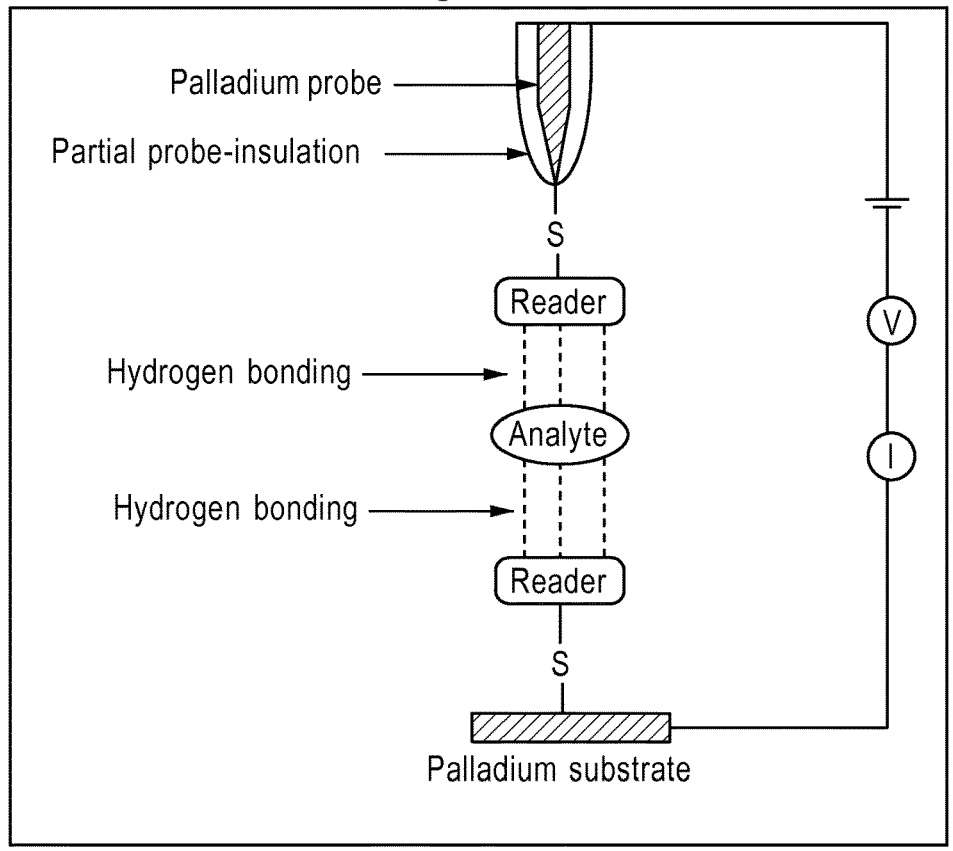
Simplified schematic diagram of STM during RT experiment
Figure 8B
Figure 8C
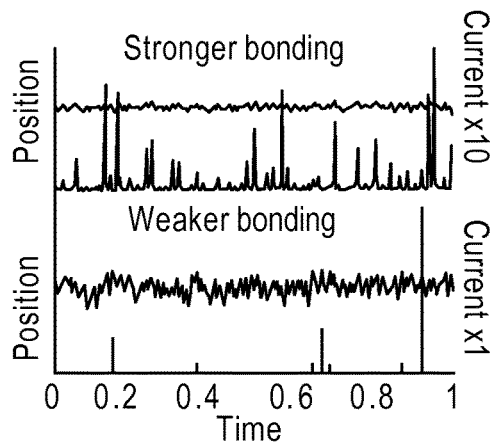
Simulated random thermal fluctuations of analytes affected by their binding strength in tunnel gap

TRIAZOLE-BASED READER MOLECULES AND METHODS FOR SYNTHESIZING AND USE THEREOF

CROSS-REFERENCE TO RELATED APPLICATIONS

This application is a national stage application under 35 U.S.C. § 371 of the International Application No. PCT/US2015/018062, filed Feb. 27, 2015 and claims priority to U.S. provisional application No. 61/945,659 titled "TRIAZOLE-BASED READER MOLECULES AND METHODS FOR SYNTHESIZING AND USE THEREOF", filed Feb. 27, 2014, the entire disclosure of which is incorporated herein by reference.

STATEMENT OF FEDERALLY SPONSORED RESEARCH

The invention(s) disclosed herein were made with government support under U54 CA143862 awarded by the National Institute of Health. The United States government has certain rights in the invention(s).

FIELD OF THE DISCLOSURE

This disclosure relates to the identification of DNA bases, sugars, proteins/peptides/amino acids, and/or pharmaceuticals (drug molecules) by means of electronic detection using recognition tunneling. Reading molecules, methods of preparing such reading molecules and methods of using the same are provided. Reading molecules, according to at least some of the embodiments of the present disclosure, may be attached to palladium surfaces/electrodes, for example, and used in the detection of single molecules and/or sequences thereof (e.g., nucleic acids, proteins, carbohydrates, and/or the like).

BACKGROUND

The human proteome, which is encoded by just some 25,000 genes, consists of millions of proteins variants, due to single nucleotide polymorphisms (SNP), somatic DNA rearrangements, RNA splicing, and post translational modifications (PTM).

In recent years, a need for a parallel method has emerged, which requires the ability to read human proteomes with high throughput and low cost. In contrast to the human genome in which DNA exists as diploid, the proteome has a wide dynamic range, for example the abundance of proteins in human plasma spans more than 10 orders of magnitude. Some proteins are expressed in a low quantity. Proteomics has no tool equivalent to the polymerase chain reaction (PCR) for protein sample amplification. There is no cost effective way to faithfully reproduce a protein population from a source. Thus, protein analysis must be carried out by extracting materials from samples removed from humans in some quantity.

There have been remarkable advances in sample preparation, and sequencing techniques, most notably based on mass spectroscopy as a proteomic tool. However, mass-spectrometers are large, costly machines. Their size is dictated by the need for very high mass resolution to obtain accurate identification of the amino acid components (and even then, readout is complicated by isobaric amino acids). Accordingly, there is a need for an alternative method for identifying amino acids, particularly in small quantities, and ideally at the single-molecule level. "Recognition Tunneling" (RT) has emerged as such a method, which is purely physical and does not rely on the reactions of a DNA polymerase or ligase, but also is able to recognize any chemical residue provided that it generates a distinctive tunneling current signal.

More specifically, the mechanism of recognition tunneling for reading nucleic acids, sugars, and amino acid sequences is based on the trapping of an analyte (i.e., a molecule of a nucleic acid, a sugar, an amino acid) by "reading molecules", which are chemically tethered to two closely spaced electrodes, which generate a distinct tunneling signal upon a potential being applied across the electrodes. Specifically, the reading molecules are chemically bonded to the metal electrodes through a short linker while non-covalently interacting with the target molecule(s) at the other end. As target molecules of nucleic acids, sugar, amino acids, drug molecules pass through the tunnel, and a potential is applied between the electrodes, interaction of each such molecule with the reading molecules temporarily traps the analytes and produces tunneling signals, which comprises a particular current. The tunneling signal can be used to identify the analytes. Prior to the present disclosure, reading molecules for RT included imidazole-based reading molecules, namely, 4(5)-(2-mercaptoethyl)-1H-imidazole-2-carboxamide (ICA) (Liang, F.; Li, S.; Lindsay, S.; Zhang, P. Chem. Eur. J. 2012, 18, 5998-6007) and 5(6)-mercapto-1H-benzo[d]imidazole-2-carboxamide (see, U.S. provisional patent application No. 61/829,229).

SUMMARY

In some embodiments, triazole-based compounds may be used as universal reader molecules for functionalization onto electrodes/substrates of RT systems. For example, triazole-based compound 5-(2-mercaptoethyl)-4H-1,2,4-triazole-3-carboxamide (TCA), the chemical structure of which can be found in FIG. 1, is a reading molecule which can be used in a RT system for the identification of an analyte containing, for example, DNA nucleotides. In some embodiments, TCA can be used to distinguish, for example, between DNA bases (including methylated cytosine), sugars, and proteins/peptides/amino acids. TCA can exist in tautomers (FIG. 2).

In some embodiments, the thickness of the triazole compound on an electrode/substrate (self assembled monolayer, or SAM) in an RT system may be between approximately 1-15 Å, and in some embodiments, between approximately 5-10 Å, and in some embodiments, between approximately about 8 and 10 Å, including all values and subranges in between. For example, a calculated thickness of the triazole compound on an electrode/substrate in a RT system was found to be about 9.90 Å (using ChemDraw3D), and according to one experiment/example, was found to be about 8.41 Å, +/−0.24 Å (thickness determined using ellipsometry). Other characterization of the triazole reader's SAM can be found with references to FIGS. 3-5.

In some embodiments, simulation of random thermal motion of analytes in tunnel gap is provided. In a strongly binding environment, analytes can experience higher fluctuations compared to an environment where analytes are weakly bonded. As a consequence of the exponential dependence of tunnel current with distance, weakly bonded analytes may give a wider range of turning current amplitude.

In some embodiments, a universal reader molecule for functionalization onto an electrode/substrate of a recognition tunneling molecule identification system are provided, which may include a triazole compound. In some embodiments, the triazole compound includes TCA.

In some embodiments, a compound of formula (I) is provided:

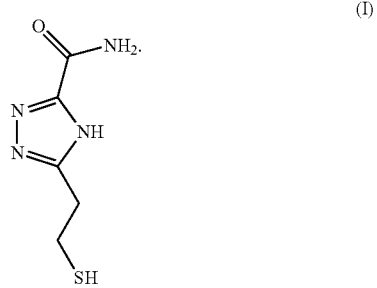 [SMILES: NC(=O)c1nnc(CCS)[nH]1]

In some embodiments, a method of using a triazole compound (e.g., TCA) as a reader molecule in a recognition tunneling molecule identification system for identifying and/or sequencing one or more individual DNA bases and/or a DNA sequence is provided.

In some embodiments, a method of using a triazole compound (e.g., TCA) as a reader molecule in a recognition tunneling molecule identification system for identifying and/or sequencing one or more individual sugars and/or a chain of sugars is provided.

In some embodiments, a method of using a triazole compound (e.g., TCA) as a reader molecule in a recognition tunneling molecule identification system for identifying and/or sequencing one or more individual amino acids and/or protein/peptide is provided.

In some embodiments, a method for preparing a triazole compound is provided which includes contacting benzyl mercaptan with 3-bromopropanenitrile in the presence of a base and a first solvent to obtain 3-(benzylthio)propanenitrile, contacting 3-(benzylthio)propanenitrile with hydrochloric gas in the presence of a second solvent to obtain benzyl 3-(benzylthio)propanimidothioate, contacting 3-(benzylthio)propanimidothioate with oxamic acid hydrazide in the presence of a third solvent to obtain 5-(2-(benzylthio)ethyl)-4H-1,2,4-triazole-3-carboxamide, and contacting 5-(2-(benzylthio)ethyl)-4H-1,2,4-triazole-3-carboxamide with sodium metal in liquid ammonia to obtain 5-(2-mercaptoethyl)-4H-1,2,4-triazole-3-carboxamide.

In some embodiments:
the first solvent may be dimethylformamide;
the base may be sodium hydride;
the second solvent may be diethyl ether; and/or
the third solvent may be pyridine.

In some embodiments a method for preparing 3-(benzylthio)propanenitrile is provided which includes contacting benzyl mercaptan with 3-bromopropanenitrile in the presence of a base. In some embodiments, the solvent is dimethylformamide. In some embodiments, the base is sodium hydride.

In some embodiments a method of preparing benzyl 3-(benzylthio)propanimidothioate is provided which includes contacting 3-(benzylthio)propanenitrile with hydrochloric gas in the presence of a solvent. In certain embodiments of this method the solvent is diethyl ether. In some embodiments a method of preparing 5-(2-(benzylthio)ethyl)-4H-1,2,4-triazole-3-carboxamide is provided which may comprise contacting 3-(benzylthio)propanimidothioate with oxamic acid hydrazide in the presence of a solvent. In certain embodiments of this method the solvent is pyridine.

In some embodiments a method of preparing 5-(2-mercaptoethyl)-4H-1,2,4-triazole-3-carboxamide is provided which includes contacting 5-(2-(benzylthio)ethyl)-4H-1,2,4-triazole-3-carboxamide with sodium metal in ammonia.

In some embodiments, a recognition tunneling system is provided which includes at least a pair of electrodes, where at least one of the electrodes includes a one or more triazole-based molecules functionalized thereto. In some embodiments, the triazole molecule includes TCA.

Such system embodiments may be used to identify and/or sequence: one or more individual DNA bases and/or DNA sequences, one or more individual carbohydrates and/or chains of sugars, and/or one or more individual amino acids and/or proteins/peptides.

BRIEF DESCRIPTION OF THE DRAWINGS

FIG. 8A is a diagram of a Recognition Tunneling measurement setup according to some embodiments of the disclosure FIGS. 8B-8C illustrate the simulated result of random thermal fluctuations of analytes in strongly (FIG. 8B) and weakly (FIG. 8C) binding in a tunnel gap.[1]

DETAILED DESCRIPTION

Figure 1:
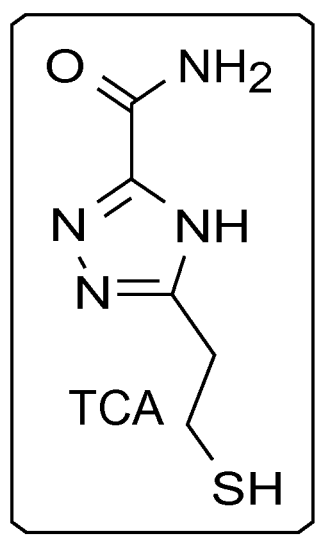
FIG. 1 is an illustration of a triazole based reading molecule 5-(2-mercaptoethyl)-4H 1,2,4-triazole-3-carboxamide (TCA), according to some embodiments of the disclosure.
Figures 2, 3:
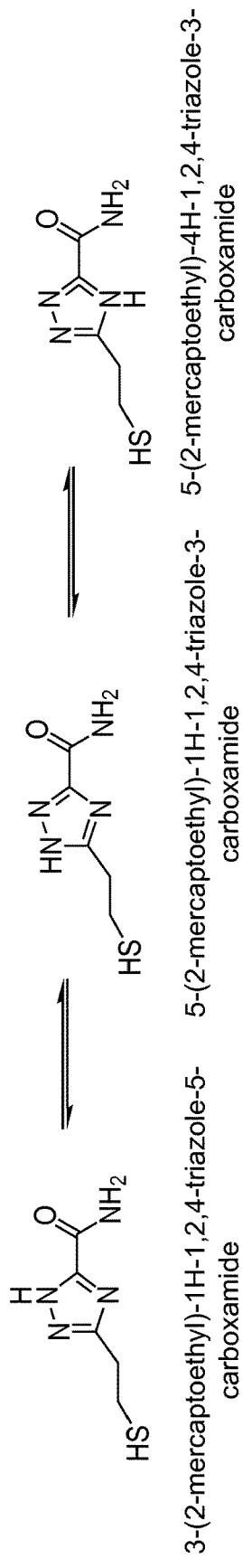
FIG. 2 is an illustration of three tautomers of the triazole-carboxamide reader, according to some embodiments of the present disclosure.
FIG. 3 is an illustration of a table showing an analysis of atomic ratio using X-ray photoelectron spectroscopy (XPS) of a SAM of TCA on a palladium substrate.
Figures 4, 5:
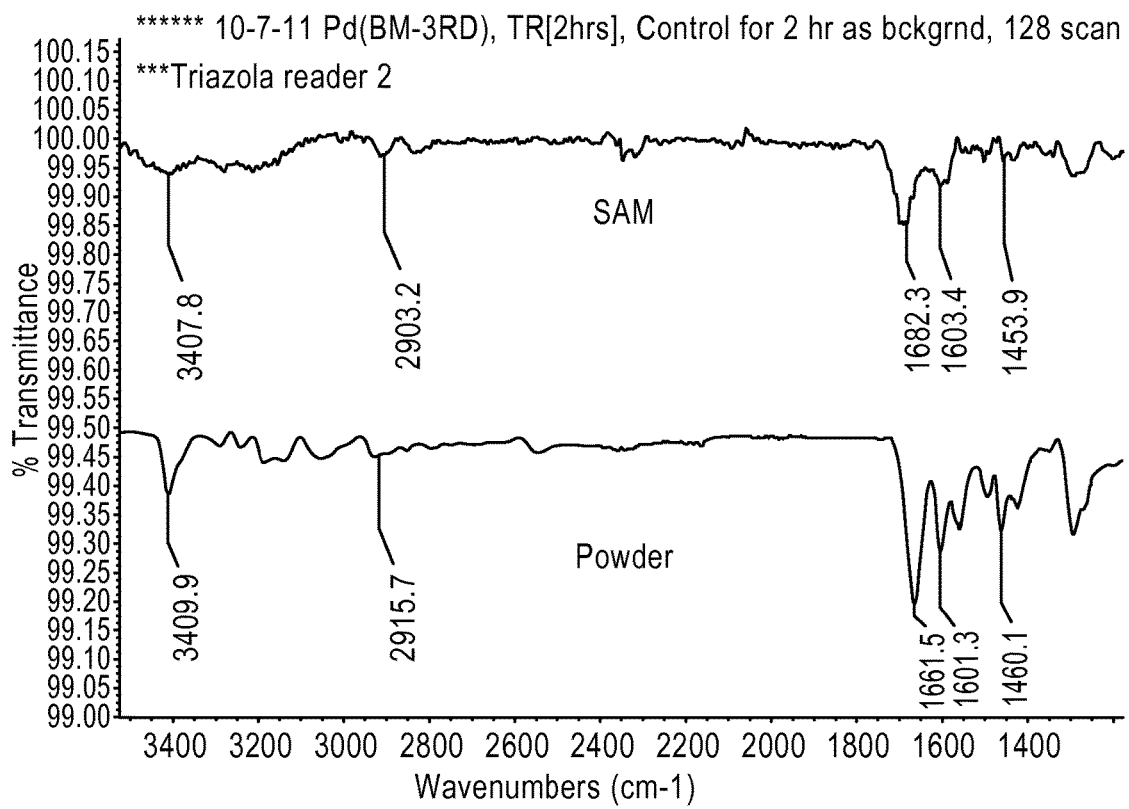
FIG. 4 is a graph of Fourier Transform Infrared Spectroscopy (FTIR) data of a SAM of TCA on a palladium substrate and TCA powder.
FIG. 5 is an illustration of measured contact angles of a SAM of TCA on a palladium substrate and a bared palladium substrate.
Figure 6:
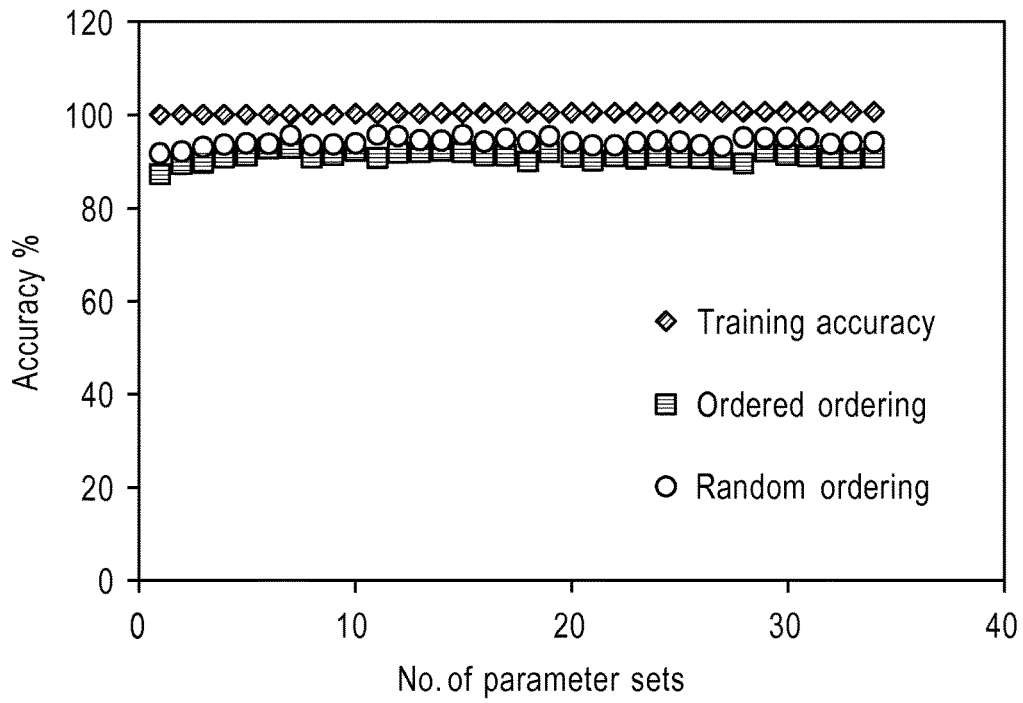
FIGS. 6-7 are charts illustrating the percent accuracy between DNA nucleotides (using support vector machine (SVM) analysis) vs. parameters for analytes for triazole (FIG. 6) and imidazole (FIG. 7).
Figure 7:
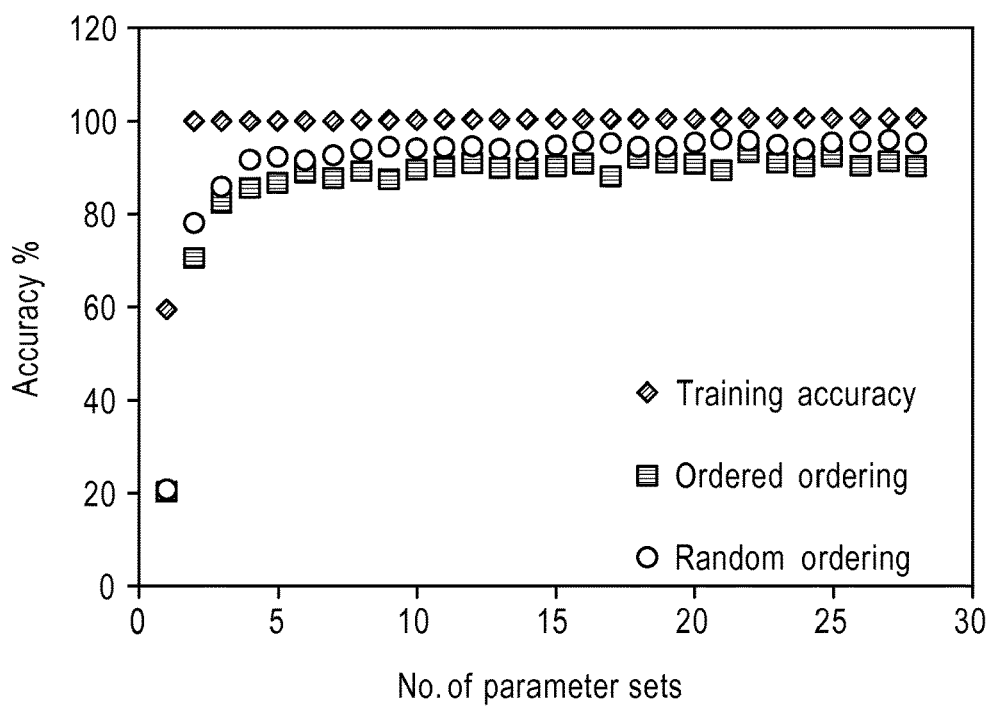
Figure 9:
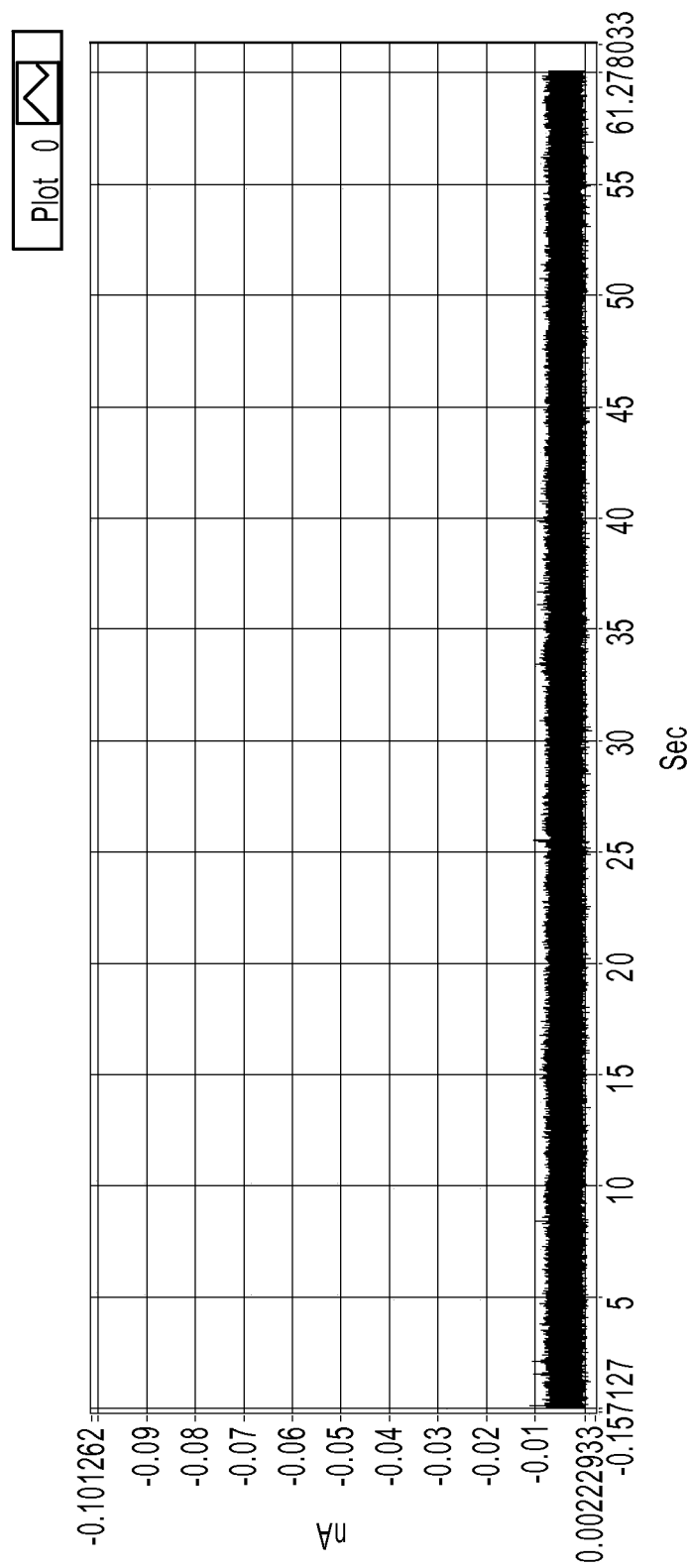
FIG. 9 is a graph showing example tunneling spectra (i.e., current spikes) obtained from a control experiment of an RT system using TCA as a molecular reader in 1 mM PB buffer
Figure 10A:
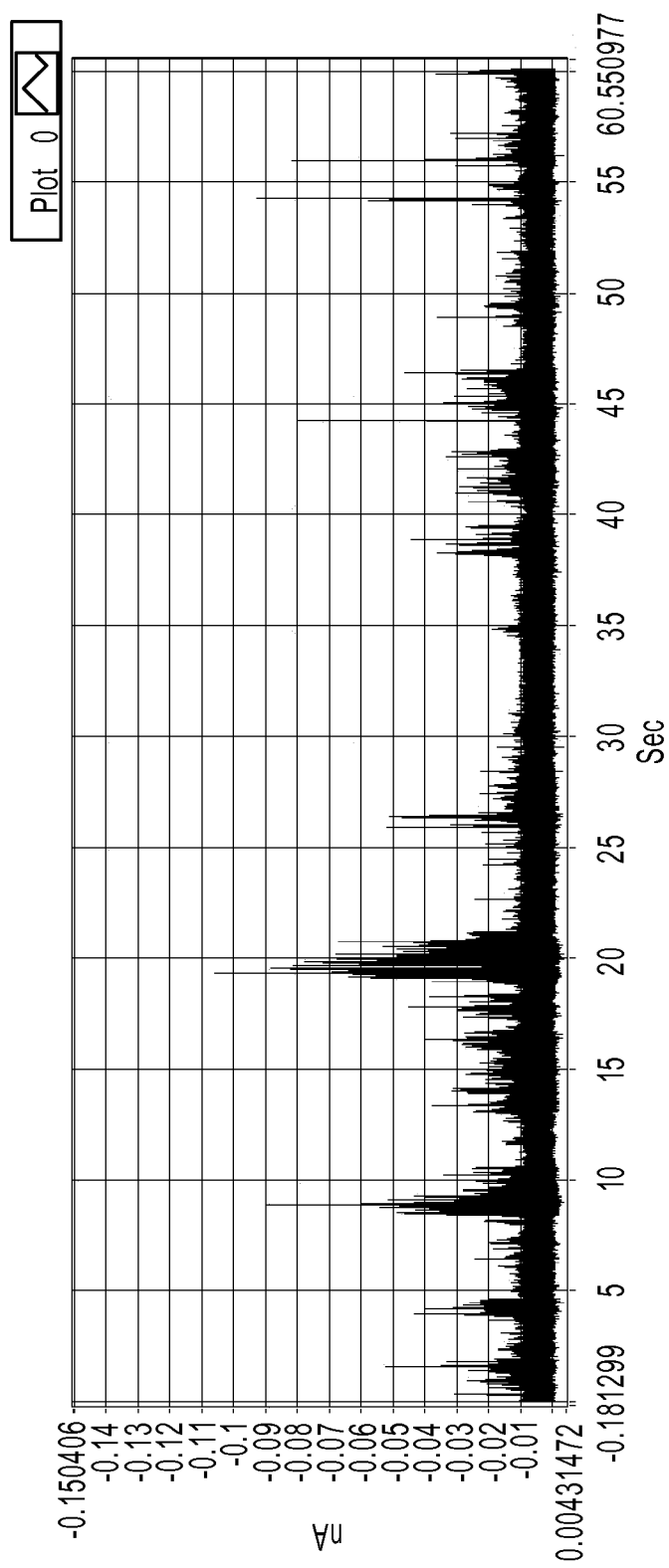
FIGS. 10A and 10B are a series of graphs is a graph of example tunneling spectra of a DNA nucleoside monophosphate dGMP obtained from an RT system using TCA as a molecular reader: 10A shows data obtained from 0-60 sec., and 10B shows data from 19.6 to 20.6 sec.
Figure 10B:
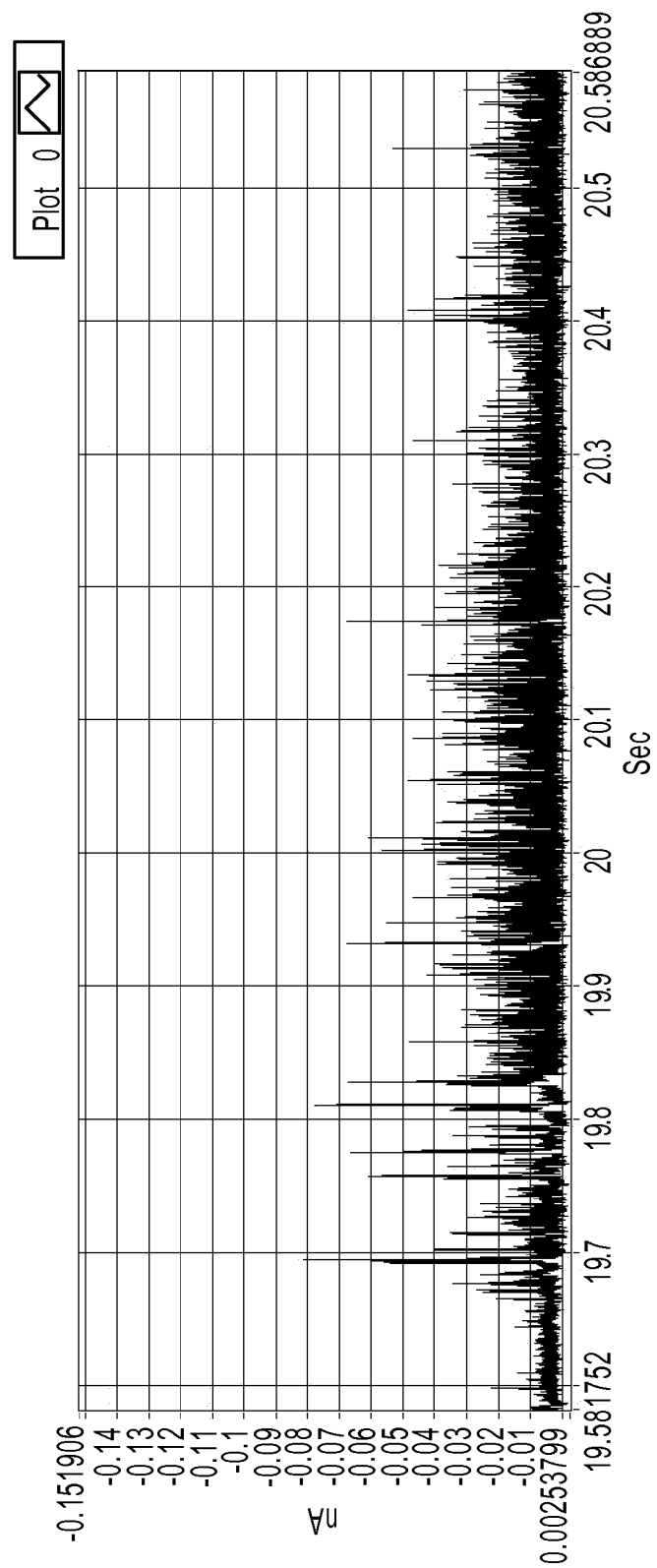
Figure 11A:
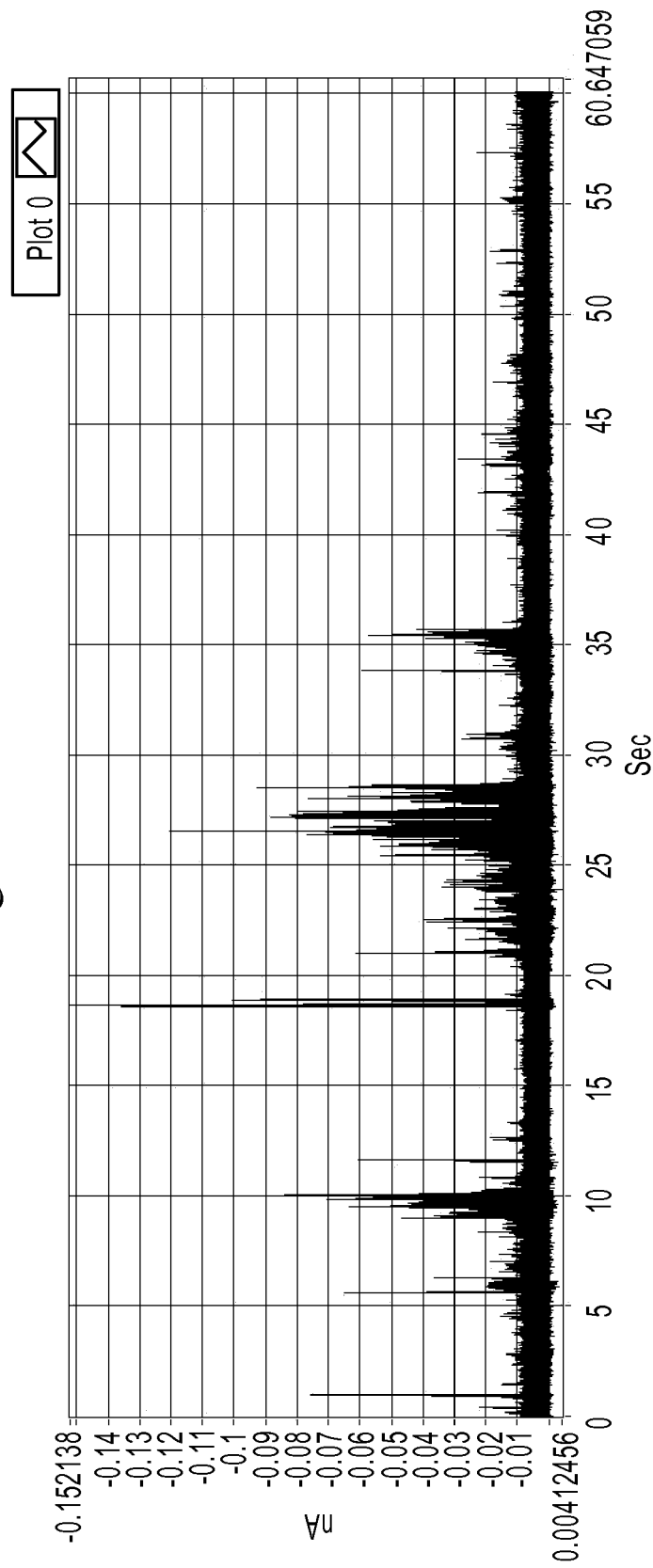
FIGS. 11A and 11B are a series of graphs of example tunneling spectra of a DNA nucleoside monophosphate dTMP obtained from an RT system using TCA as a molecular reader: 11A shows data obtained from 0-60 sec., and 11B shows data from 26.4 to 27.4 sec.
Figure 11B:
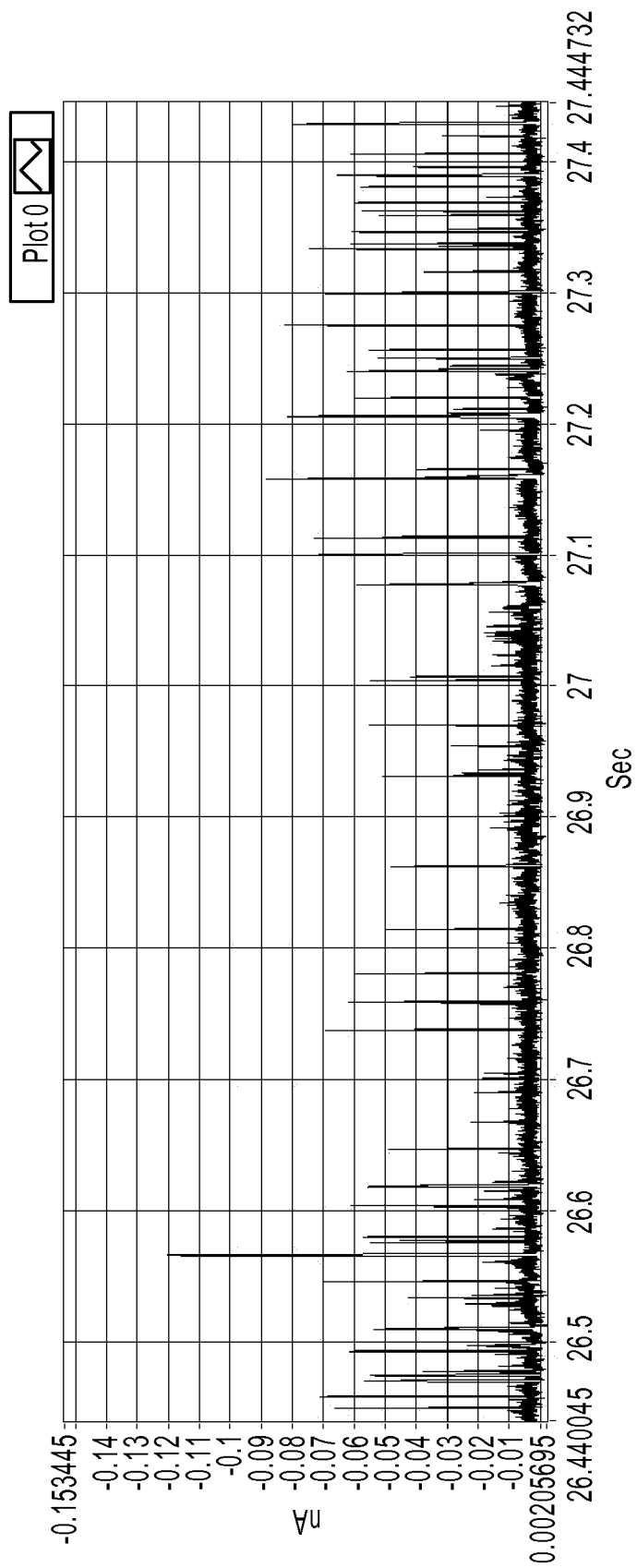
Figure 12A:
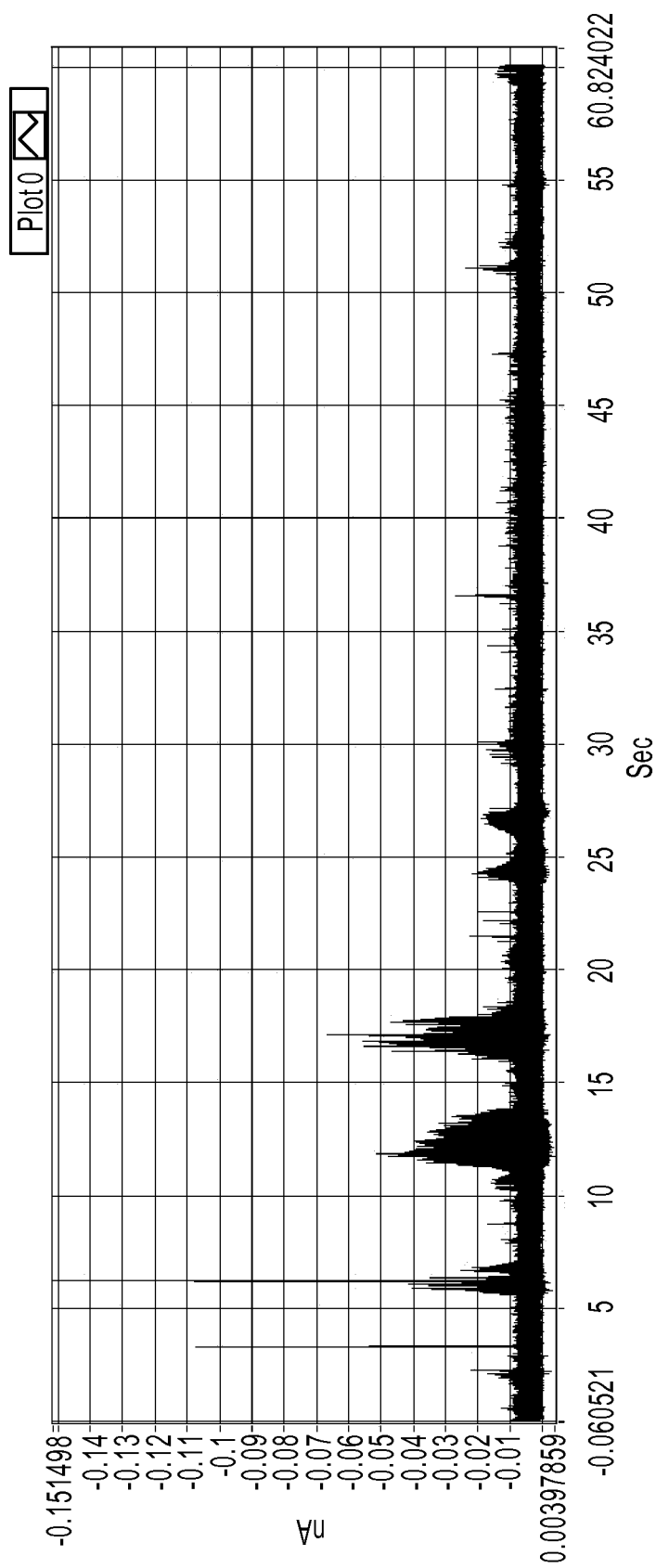
FIGS. 12A and 12B are a series of graphs of example tunneling spectra of a DNA nucleoside monophosphate dAMP obtained from an RT system using TCA as a molecular reader: 12A shows data obtained from 0-60 sec., and 12B shows data from 11.3 to 12.3 sec.
Figure 12B:
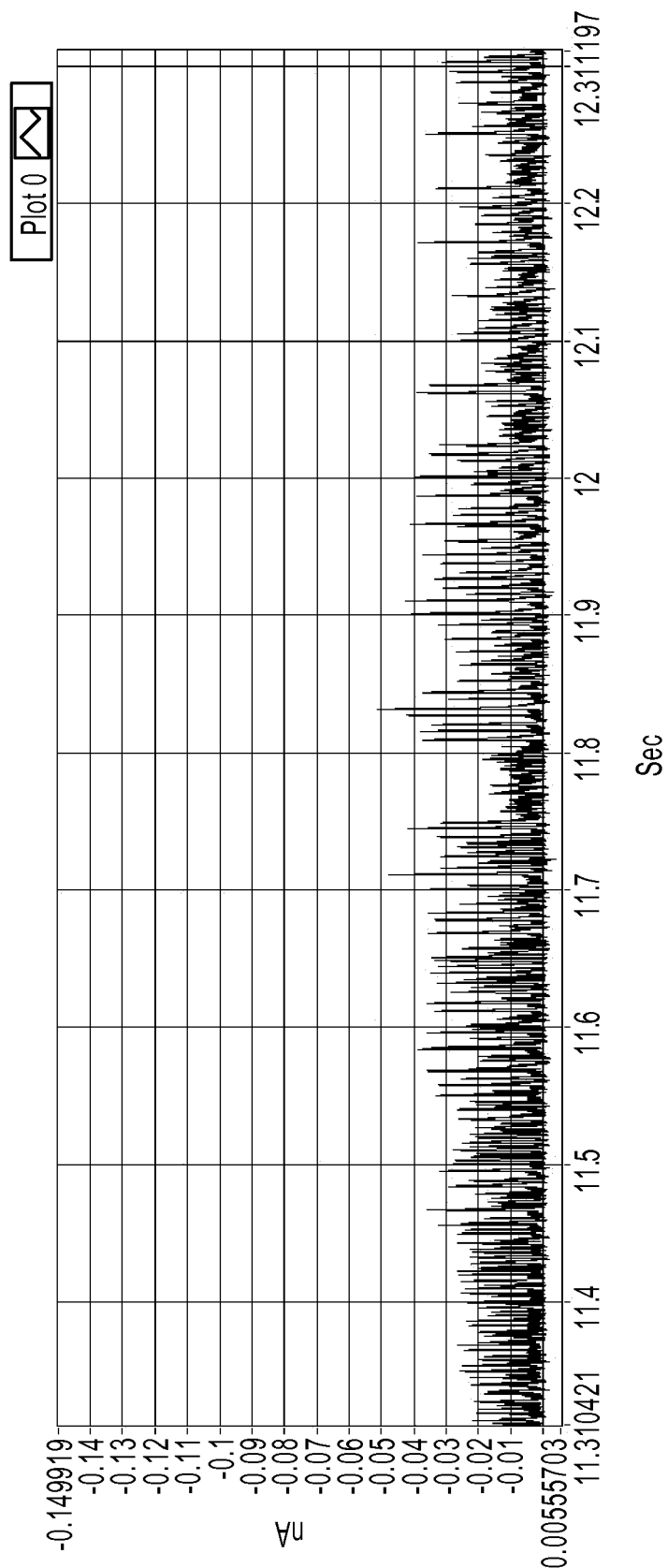
Figure 13A:
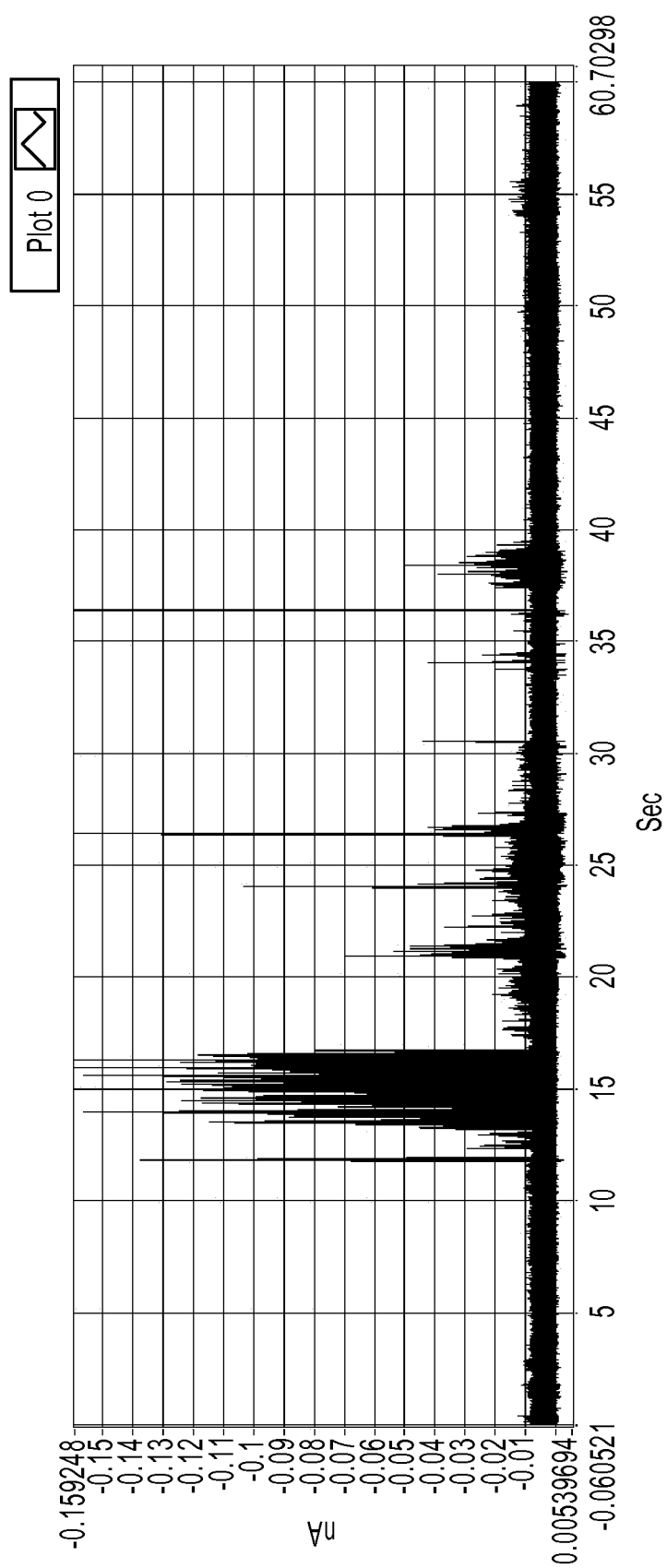
FIGS. 13A and 13B are a series of graphs of example tunneling spectra of a DNA nucleoside monophosphate dCMP obtained from an RT system using TCA as a molecular reader: 13A shows data obtained from 0-60 sec., and 13B shows data from 14.3 to 15.3 sec.
Figure 13B:
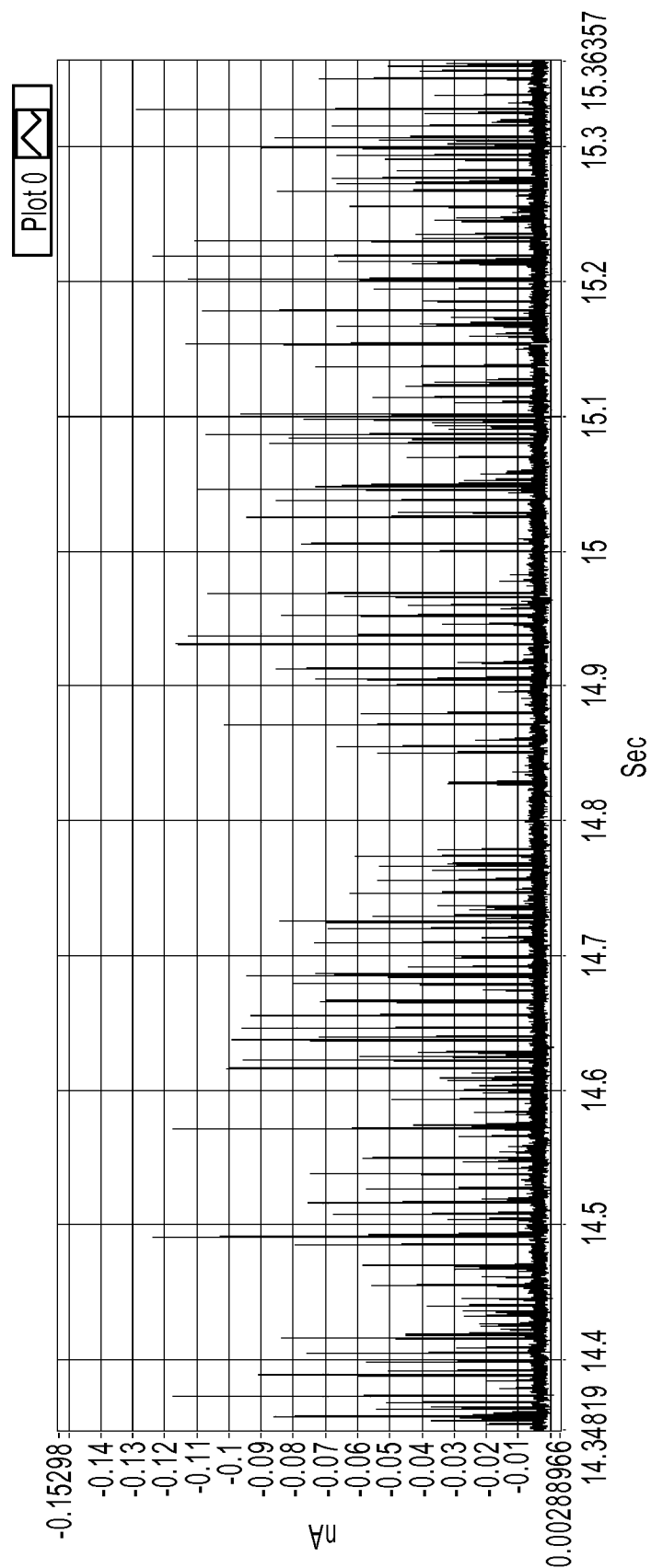
Figure 14A:
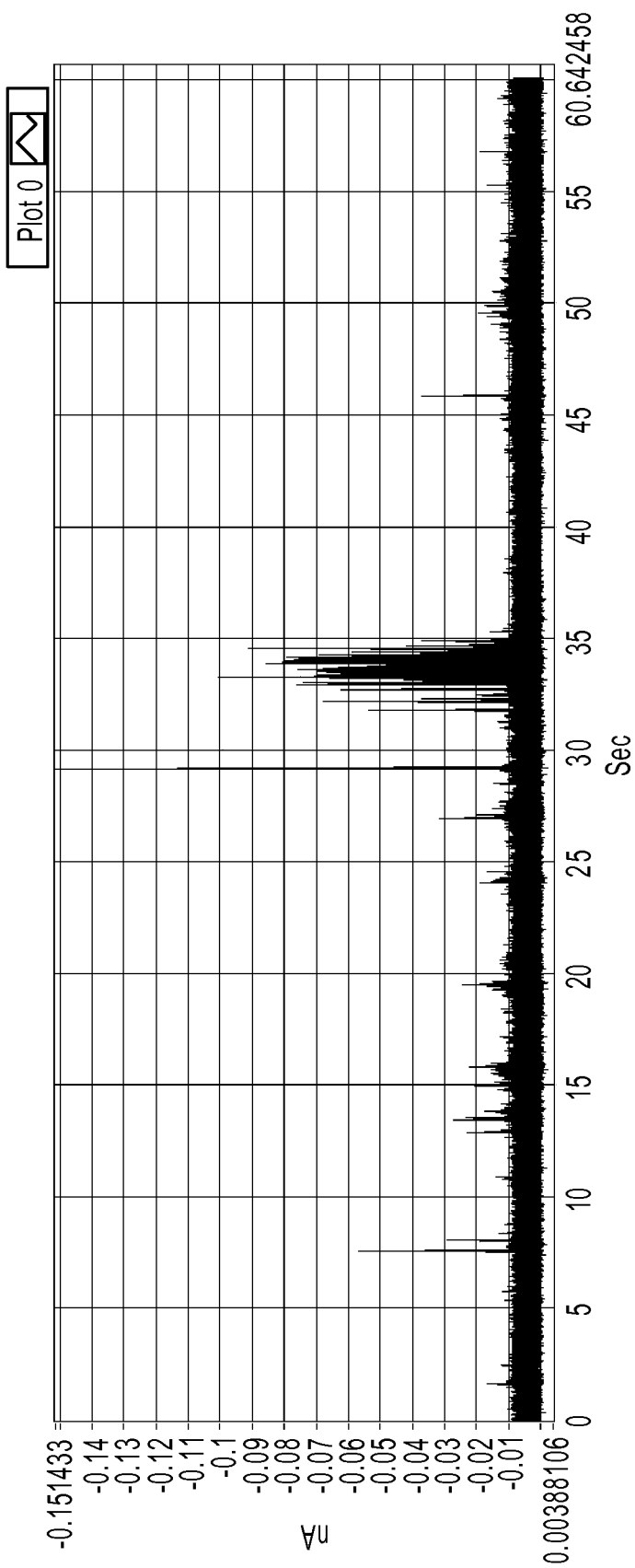
FIGS. 14A and 14B are a series of graphs of example tunneling spectra of a DNA nucleoside monophosphate 5-methyl-dCMP obtained from an RT system using TCA as a molecular reader: 14A shows data obtained from 0-60 sec., and 14B shows data from 33.18 to 34.18 sec.
Figure 14B:
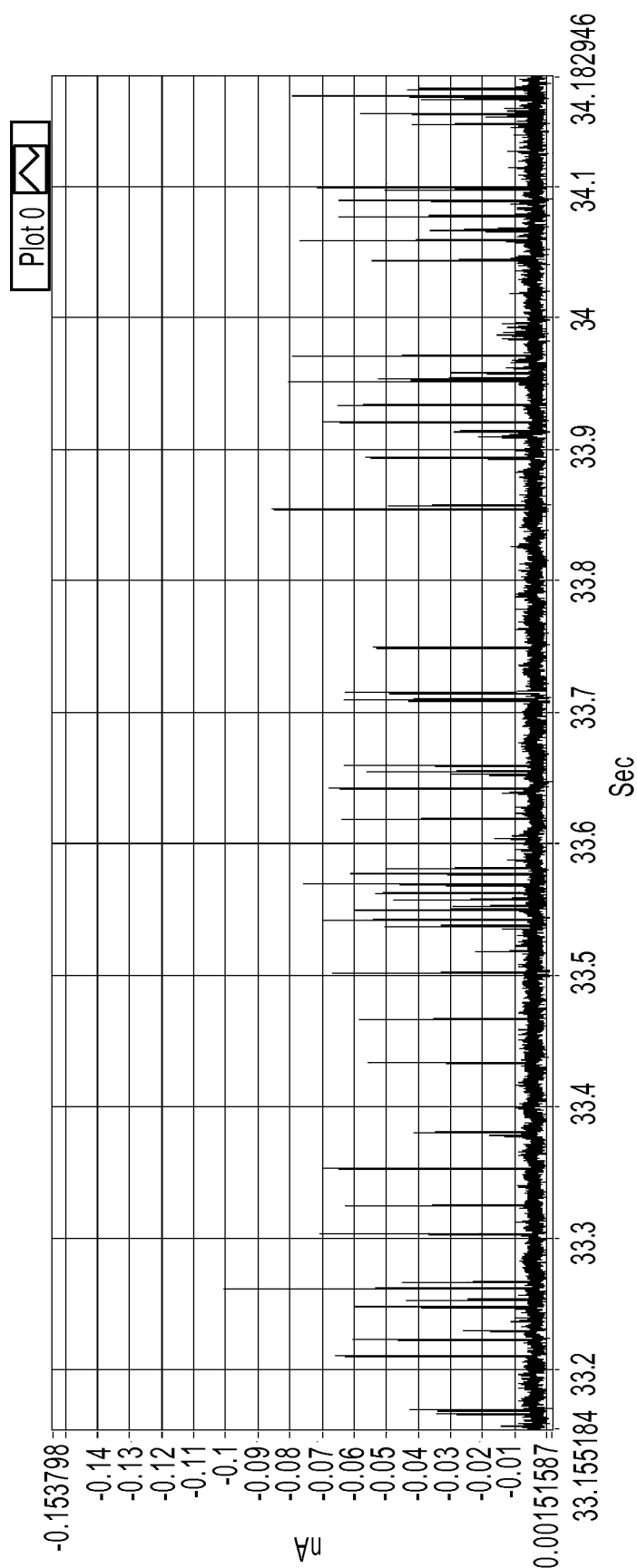

Some embodiments include triazole-containing reading molecules which improve the ability for reading DNA bases over, for example, imidazole-based reading molecules in an RT apparatus. Such improvements can be attributed to, for example, a lesser number of parameters to reach a level of (for example) 95.5% accuracy to distinguish different nucleoside monophosphates. This can be seen, for example, with reference to FIGS. 6-7, charts which illustrate the percent accuracy between DNA nucleosides (using support vector machine (SVM) analysis) vs. parameters for analytes for both TCA (FIG. 6) and ICA (FIG. 7). As one of ordinary skill in the art will appreciate, the triazole reader molecules provide similar accuracy with a lesser number of parameters.

The triazole-based reading molecules may also interact with carbohydratees (e.g. galactose), as evident with their interaction with DNA bases, as well as with amino acids.

FIG. 8A illustrates a substrate and tunneling measurement (STM) instrument used for the recognition tunneling measurements, which includes of a sample stage/plate with a teflon liquid cell, scanner and microscope head. Prior to an STM measurement, the teflon cell was cleaned with freshly prepared piranha solution (a 3:1 mixture of sulfuric acid and hydrogen peroxide), followed by sonication in nanopure water three (3) times and in ethanol three (3) times, then blow-dry with nitrogen. The functionalized palladium tip and palladium substrate were rinsed thoroughly with ethanol, and blow-dried with nitrogen. A new tip and substrate set was used for each experiment for different DNA monophosphates. The same procedure was followed for immobilization of triazole reader as was done for imidazole reader immobilization.

Initially, for an STM measurement, the tip was inserted into the scanner and connected to the microscope head. The voltage was adjusted to zero by using the adjustment screw on the top of the scanner while checking the oscilloscope, to measure the variation voltage or other electrical signal as a function of time. Voltage was also adjusted to zero (e.g., via picoview software). Labview software was used for tracking, recording and further analysis of current signal as a function of time. Before starting the measurement, the oscilloscope, the picoview and the Labview software should all be reading 0 V applied bias (voltage) and 0 pA current. A sodium phosphate buffer (10 mM, pH 7.0, 120 uL) was added to the teflon cell. The value of leakage current with an applied bias of (−0.5 V) was checked, keeping the tip far enough from the surface of the palladium substrate (i.e., not in tunneling regime). The tip was discarded if the value was more than 1 pA. All measurements were done with tips having a leakage current below 1 pA. After the leakage check, the tip was made to approach the bottom electrode until the tunneling current reached 2 pA (also termed as "set point") under an applied bias of (−0.5V) and definite set of values for I gain and P gain (1=1.5, P=1.5) in picoview.

After the tip engaged, a few STM images were taken to verify that the tip was not over-coated. After a well defined image of the palladium substrate was obtained, the tip was withdrawn for 20 microns and the system was stabilized for 2 hours. Then the tip was arranged adjacent to the surface (2 pA set point, −0.5 V bias, 1=1.5, P=1.5). Both I and P values were changed to 0.1, and then control data was recorded at two different values of set point (2 pA & 4 pA). Thereafter, the tip was withdrawn and the phosphate buffer was discarded carefully, followed by the addition of a DNA monophosphate solution (100 μM) to the liquid cell. The tip was then arranged in the same manner and withdrawn for 20 microns prior to system stabilization of 2 hours. After 2 hours, the tip was arranged again and the tunneling data of the DNA monophosphates was recorded at two different values of set point (2 pA & 4 pA). The data were then analyzed using support vector machine (SVM) analysis.

Figure 15A:
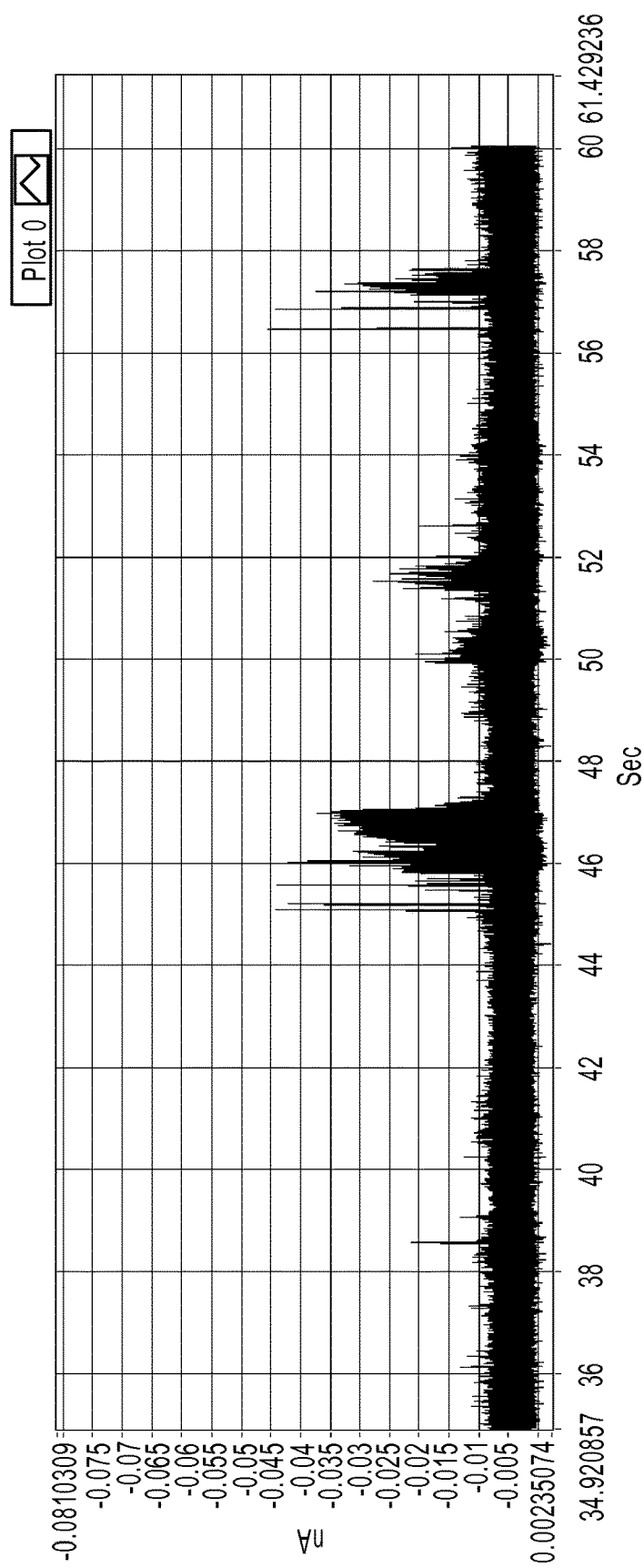
FIGS. 15A and 15B are a series of graphs of example tunneling spectra of a sugar molecule galactose obtained from an RT system using TCA as a molecular reader: 15A shows data obtained from 0-60 sec., and 15B shows data from 45.64 to 47.99 sec.
Figure 15B:
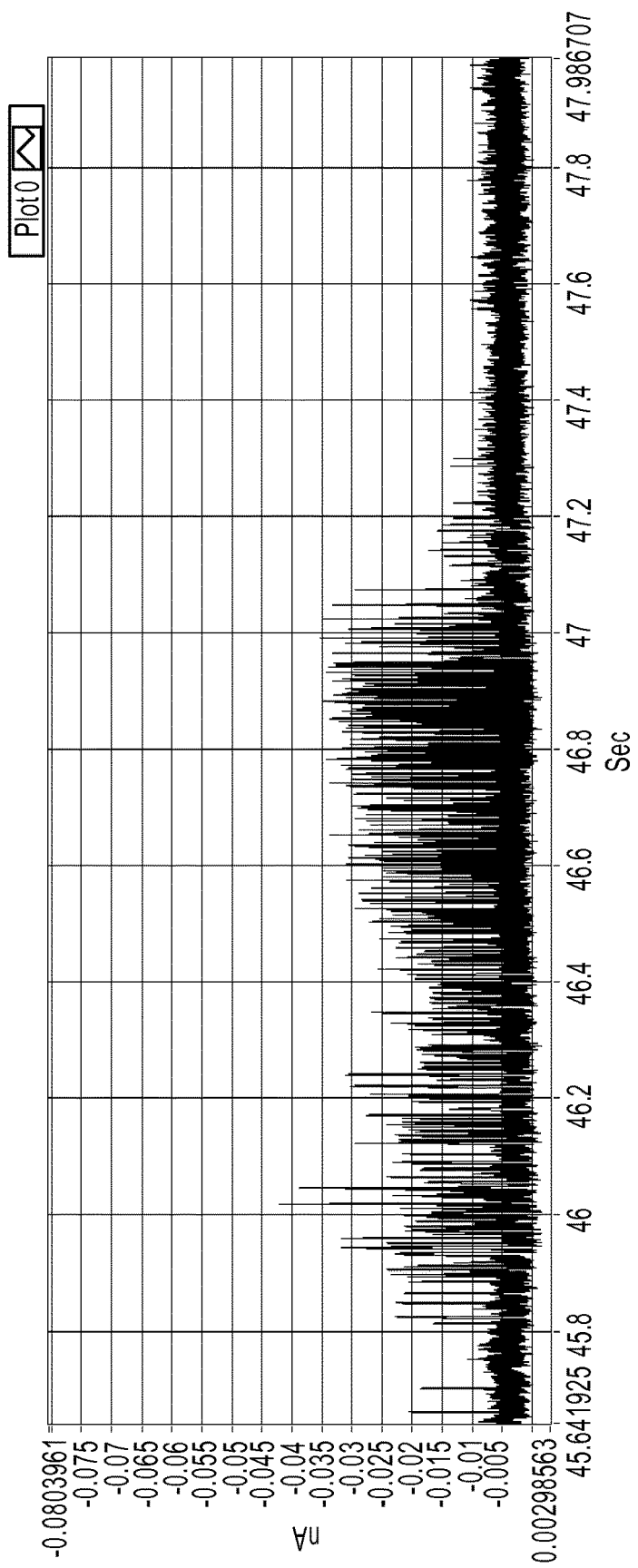

FIGS. 10A-14B are graphs illustrating example tunneling current spikes for different DNA nucleotides. FIGS. 15A-B are graphs illustrating example tunneling current spikes of a sugar molecule (galactose).

Synthesis of a Triazole-Based Universal Reading Molecule

Figure 16:
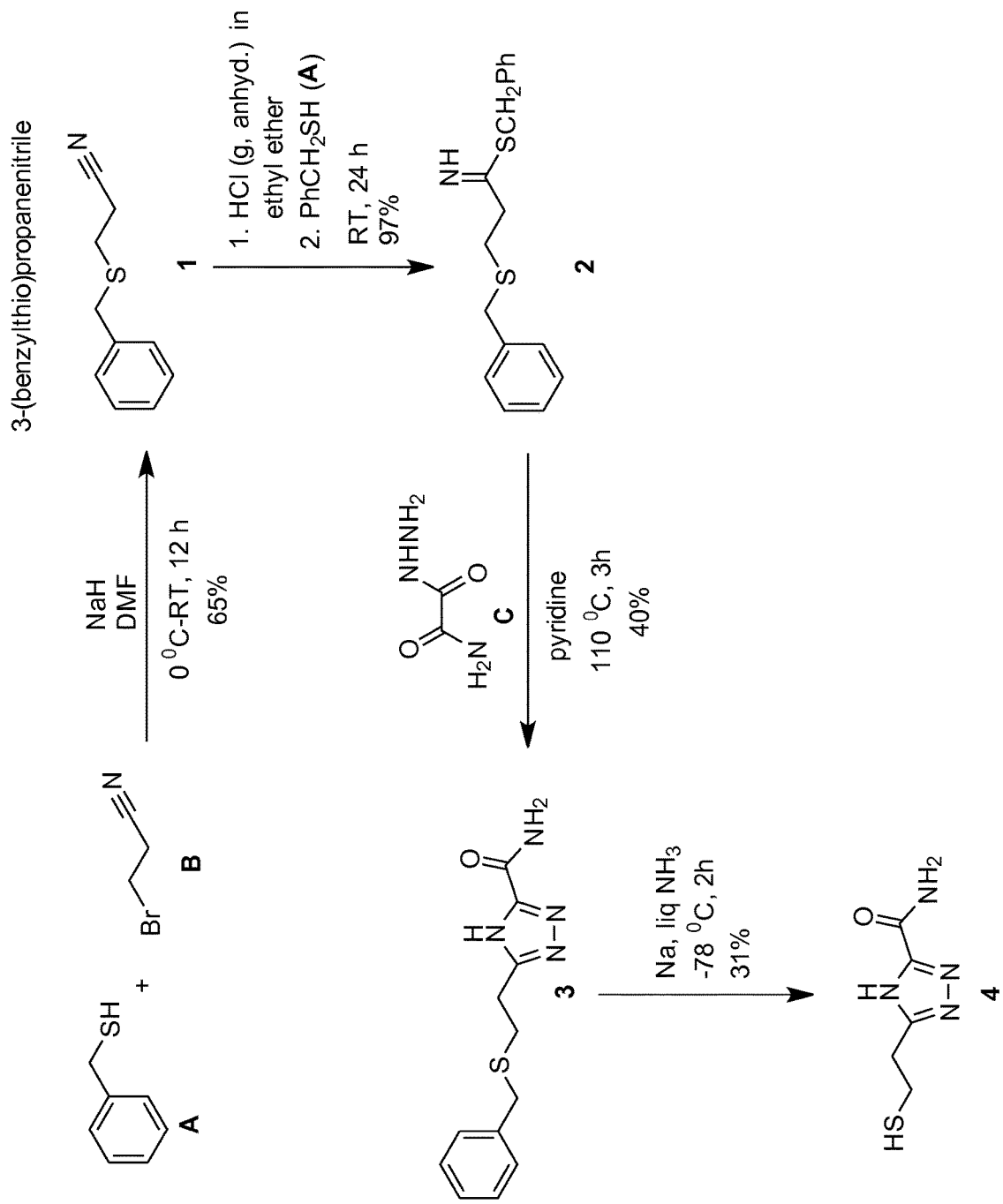
FIG. 16 is an illustration of a reaction scheme, according to some embodiments, for the synthesis/preparation of TCA.

In some embodiments, methods for synthesizing triazole-based compounds are provided. The synthesized triazole-based compounds may be used as a universal reader molecule in a recognition tunneling molecule identification system (see above). For example, in some embodiments, such a method for synthesizing the triazole compound 5-(2-mercaptoethyl)-4H-1,2,4-triazole-3-carboxamide (TCA) is provided. Such an example method is outlined in FIG. 16, with reference to the following compounds:

(1) 3-(benzylthio)propanenitrile (2) 3-(benzylthio)propanimidothioate (Lunt, E.; Newton, C., G.; Smith, C.; Stevens, G., P.; Stevens, M., F., G.; Straw, C., G.; Walsh, R., J., A.; Warren, P., J.; Fizames, C.; Lavelle, F.; Langdon, S., P.; Vickerss, L., M. *J. Med. Chem.* 1987, 30, 357-366)

(3) 5-(2-(benzylthio)ethyl)-4H-1,2,4-triazole-3-carboxamide (Chudinov, M., V.; Konstantinova, I., I).; Ryzhova, O., I.; Esipov, R., S.; Yurkevich, A., M.; Shvets, V., I.; A., I. *Pharmaceutical Chemistry Journal,* 2005, 39, 212-215)

(4) 5-(2-mercaptoethyl)-4H-1,2,4-triazole-3-carboxamide (Liang, F.; Li, S.; Lindsay, S.; Zhang, P. *Chem. Eur. J.* 2012, 18, 5998-6007)

In some embodiments, (1) is synthesized and then used to synthesize (2), which is then in turn synthesized to synthesize (3), which is then used to synthesize (4).

Example: Synthesis of 3-(benzylthio)propanenitrile (Product 1)

Benzyl mercaptan A (1.05 g, 19.0 mmol) was added into a stirred solution of sodium hydride (60% in mineral oil, 1.16 g, 24.0 mmol) in anhydrous DMF (50 mL) at 0° C. under nitrogen. After the addition was complete, the reaction mixture was stirred for another 30 min, followed by the slow addition of 3-bromopropanenitrile B (2.68 g, 20.0 mmol). The resulting mixture was allowed to warm at room temperature, stirred for 12 hours until benzyl mercaptan was consumed. The solvent was removed by rotary evaporation, followed by addition of a saturated $NH_4Cl$ aqueous solution (20 mL), and extracted with chloroform (3×20 mL). The combined organic extracts were washed with brine (30 mL), and dried over magnesium sulfate. The solution was then filtered and concentrated by rotary evaporator. The crude product was purified by silica gel flash column chromatography. 3-(Benzylthio)propanenitrile (Product 1) was obtained as pale yellow liquid (2.25 g, 65%). $^1$H NMR (400 MHz, CDCl$_3$): δ=7.24-7.33 (5H, m, ArH), 3.78 (2H, s, PhCH$_2$), 2.64 (2H, t, J=8.0 Hz, CH$_2$), 2.47 ppm (2H, t, J=8.0 Hz, CH$_2$); $^{13}$C NMR (100 MHz, CDCl$_3$): δ=137.2, 128.9, 127.2, 118.3, 36.0, 26.2, 18.3 ppm; HRMS (APCI+): m/z calculated for C$_{10}$H$_{11}$NS+H: 178.0690; found: 178.0688.

Example: Synthesis of benzyl 3-(benzylthio)propanimidothioate from 3-(benzylthio)propanenitrile (Product 2)

Product 1 (2.0 g, 11.3 mmol) and benzyl mercaptan (2.0 mL, 16.93 mmol) were added subsequently into anhydrous ethyl ether (120 mL) under nitrogen. The resulting solution was cooled in an ice bath, and HCl (gas, anhydrous) was bubbled into it for 2 h. It was stirred for 24 h at room temperature. Then it was left unstirred for another 2 h. The product was crystallized in the reaction mixture, and filtered through a Buchner funnel. The crystals were washed with three portions (each 20 mL) of cold ethyl ether and dried in vacuum. Product 2 was obtained as white crystals (3.7 g, 97%). $^1$H NMR (400 MHz, CDCl$_3$): δ=7.21-7.38 (10H, m, ArH), 4.78 (2H, s, CSCH$_2$Ph), 3.86 (2H, s, PhCH$_2$S—CH$_2$), 3.20 (2H, t, J=7.2 Hz, SCH$_2$—), 2.88 (2H, t, J=7.2 Hz, —CH$_2$—), 1.61 ppm (1H, s, broad, NH); $^{13}$C NMR (100 MHz, CDCl$_3$): δ=193.3, 137.8, 131.3, 129.8, 129.6, 129.4, 129.3, 129.0, 127.6, 39.3, 37.5, 36.3, 29.7 ppm; HRMS (APCI+): m/z calculated for C$_{17}$H$_{19}$NS$_2$+H: 302.1037; found: 302.1036.

Example: Synthesis of 5-(2-(benzylthio)ethyl)-4H-1,2,4-triazole-3-carboxamide from 3-(benzylthio) propanimidothioate (Product 3)

Oxamic acid hydrazide C (0.34 g, 3.32 mmol) was added into a solution of product 2 (1.0 g, 3.32 mmol) in anhydrous pyridine (10 mL) at room temperature. The resulting solution was refluxed at 110° C. for 3 h. Pyridine was removed by co-evaporating with toluene (5 mL×2) using a rotary evaporator to obtain yellow gummy liquid. DMSO (15 mL) was added to just dissolve the crude and sufficient water (50 mL) was added to get white precipitate, which was filtered through a Buchner funnel and washed thoroughly with cold water (40 mL), followed by cold ethyl ether (40 mL). The solid was dried in vacuum to obtain 0.53 g of a crude product, which was then recrystallized from boiling ethanol (25 mL), filtered, and dried in vacuum at 40° C. to furnish product 3 as white crystals (0.31 g, 40%). $^1$H NMR (400 MHz, DMSO-d$_6$): δ=7.81 (1H, s, broad, —NH$_2$), 7.58 (1H, s, broad, —NH$_2$), 7.18-7.28 (5H, m, ArH), 3.70 (2H, s, PhCH$_2$—), 2.93 (2H, t, J=7.2 Hz, —CH$_2$), 2.73 ppm (2H, t, J=7.2 Hz, —CH$_2$); $^{13}$C NMR (100 MHz, DMSO-d$_6$): δ=160.4, 138.8, 129.2, 128.8, 127.3, 35.3, 29.1, 27.2 ppm; HRMS (APCI+): m/z calculated for C$_{12}$H$_{14}$N$_4$OS+H: 263.0967; found: 263.0972.

Example: Synthesis of 5-(2-mercaptoethyl)-4H-1,2,4-triazole-3-carboxamide from 5-(2-(benzylthio) ethyl)-4H-1,2,4-triazole-3-carboxamide (Product 4)

Product 3 (150 mg, 0.572 mmol) was added into liquid ammonia (2 mL) at −78° C. and stirred for 15 min. Small pieces of freshly cut sodium were added into the solution until a blue color remained unchanged for about 3 min. Then NH$_4$Cl was added to quench the reaction until the blue color disappeared. Ammonia was allowed to evaporate under nitrogen flow at room temperature. For separation, the residue was dissolved in methanol, followed by the addition of silica gel. The solvent was removed by rotary evaporation. The crude product was purified by silica gel flash column chromatography while the pure product was eluted out with a gradient of methanol (0 to 10% in 2 h) in dichloromethane. Product 4 was obtained as white solid (98 mg, 31%). $^1$H NMR (400 MHz, DMSO-d$_6$): δ=6.79 (1H, s, broad, —NH$_2$), 6.71 (1H, s, broad, —NH$_2$), 2.57 (2H, t, J=6.8 Hz, —CH$_2$); 2.43 (2H, t, J=6.8 Hz, —CH$_2$), 2.08 (1H, t, J=2.0 Hz, —SH); HRMS (APCI+): m/z calculated for C$_5$H$_8$N$_4$OS+H: 173.0497; found: 173.0493.

Any and all references to publications or other documents, including but not limited to, patents, patent applications, articles, webpages, books, etc., presented in the present application, are herein incorporated by reference in their entirety.

Although a few variations have been described in detail above, other modifications are possible. For example, any logic flow depicted in any figure and/or described herein does not require the particular order shown, or sequential order, to achieve desirable results. Other implementations may be within the scope of at least some of the following exemplary claims.

Example embodiments of formulations and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include formulations, methods, systems and devices which may further include any and all elements from any other disclosed methods, systems, and devices, including any and all elements corresponding to triazole reader molecules and RT systems incorporating such reader molecules. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure).

What is claimed is:

1. A universal reader molecule for functionalization onto electrodes of a recognition tunneling molecule identification system comprising a triazole carboxamide compound of 5-(2-mercaptoethyl)-4H-1,2,4-triazole-3-carboxamide and its tautomers.

2. A compound of formula (1)

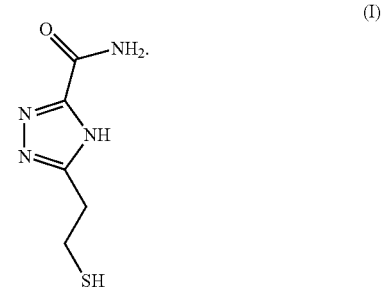 [SMILES: NC(=O)c1nnc(CCS)[nH]1]

3. A method for preparing a triazole compound of claim 2, comprising:

contacting benzyl mercaptan with 3-bromopropanenitrile in the presence of a base and a first solvent to obtain 3-(benzylthio)propanenitrile;

contacting 3-(benzylthio)propanenitrile with hydrochloric gas in the presence of a second solvent to obtain benzyl 3-(benzylthio)propanimidothioate;

contacting 3-(benzylthio)propanimidothioate with Oxamic acid hydrazide in the presence of a third solvent to obtain 5-(2-(benzylthio)ethyl)-4H-1,2,4-triazole-3-carboxamide; and contacting 5-(2-(benzylthio)ethyl)-4H-1,2,4-triazole-3-carboxamide with sodium metal and ammonia to obtain 5-(2-mercaptoethyl)-4H-1,2,4-triazole-3-carboxamide.

4. The method of claim 3, wherein the first solvent is dimethylformamide, the second solvent is diethyl ether, the base is sodium hydride, and the third solvent is pyridine.

5. The method of claim 3, wherein the base is sodium hydride.

6. The method of claim 3, wherein the second solvent is diethyl ether.

7. The method of claim 3, wherein the third solvent is pyridine.

8. A recognition tunneling system comprising at least a pair of electrodes with at least one of which having one or more triazole-based molecules functionalized thereto, wherein the one or more triazole-based molecules comprises 5-(2-mercaptoethyl)-4H-1,2,4-triazole-3-carboxamide.

9. The system of claim 8, wherein the triazole molecule comprises 5-(2-mercaptoethyl)-4H-1,2,4-triazole-3-carboxamide and its tautomers.

10. The system of claim 8, wherein the system is configured to identify a sequence of one or more individual DNA bases.

11. The system of claim 8, wherein the system is configured to identify a sequence of one or more individual sugars, chains of sugars, or oligo- and poly-saccharides.

12. The system of claim 8, wherein the system is configured to identify a sequence of one or more individual amino acids or proteins/peptides.

* * * * *